US009565858B2

(12) United States Patent
Ijaz et al.

(10) Patent No.: US 9,565,858 B2
(45) Date of Patent: Feb. 14, 2017

(54) AQUEOUS ALCOHOLIC MICROBICIDAL COMPOSITIONS COMPRISING ZINC IONS

(71) Applicant: Reckitt Benckiser LLC, Parsippany, NJ (US)

(72) Inventors: Mohammad Khalid Ijaz, Montvale, NJ (US); Yun-Peng Zhu, Fairlawn, NJ (US)

(73) Assignee: RECKITT BENCKISER LLC, Parsippany, NJ (US)

( * ) Notice: Subject to any disclaimer, the term of this patent is extended or adjusted under 35 U.S.C. 154(b) by 0 days.

(21) Appl. No.: 14/410,184

(22) PCT Filed: Jun. 28, 2013

(86) PCT No.: PCT/GB2013/051724

§ 371 (c)(1),
(2) Date: Dec. 22, 2014

(87) PCT Pub. No.: WO2014/006382

PCT Pub. Date: Jan. 9, 2014

(65) Prior Publication Data

US 2015/0189888 A1 Jul. 9, 2015

Related U.S. Application Data

(60) Provisional application No. 61/731,940, filed on Nov. 30, 2012.

(30) Foreign Application Priority Data

Jul. 2, 2012 (GB) .................................. 1211701.6

(51) Int. Cl.
*A01N 25/00* (2006.01)
*A01N 59/16* (2006.01)
*A01N 31/02* (2006.01)
*A01N 33/12* (2006.01)

(52) U.S. Cl.
CPC ............... *A01N 59/16* (2013.01); *A01N 31/02* (2013.01); *A01N 33/12* (2013.01)

(58) Field of Classification Search
None
See application file for complete search history.

(56) References Cited

U.S. PATENT DOCUMENTS 2,118,225 A 5/1938 Pierce
3,282,776 A 11/1966 Kitzke et al.
3,835,057 A 9/1974 Wai Ming Cheng et al.
4,098,602 A 7/1978 Seymour et al.
4,198,296 A 4/1980 Doumas et al.
4,407,818 A 10/1983 Lionelle et al.
4,477,438 A 10/1984 Willcockson et al.
4,647,458 A 3/1987 Ueno et al.
4,654,213 A 3/1987 Ramirez et al.
4,678,658 A 7/1987 Casey et al.
4,695,453 A 9/1987 Tuominen et al.
4,714,563 A 12/1987 Kajs et al.
4,793,988 A 12/1988 Casey et al.
(Continued)

FOREIGN PATENT DOCUMENTS

EP 0079579 A1 11/1982
EP 0099209 A1 6/1983
(Continued)

OTHER PUBLICATIONS

International Search Report and Written Opinion of the International Searching Authority for PCT/GB2013/051724 dated Sep. 2, 2013.
GB Search Report for GB1211701.6 dated Nov. 1, 2012.
N. Kida, et al., "Synergistic effect of ethanol on the pH dependent preferential antibacterial-activity og ethylenediaminetetraacetic acid (EDTA) against gram negative bacilli", Abstract, Nippon Bokin Bobai Gakkai, STN Database Accession No. 2000: 31926, XP-002197632, Japan 1999.
C.E.Coulthard, et al., "The Germicidal Effect of Alcohol with Special Reference to its Action on Bacterial Spores", The Pharmaceutical Journal, Jul. 18, 1936, pp. 79-81.
Anonymous, "Disinfectant", Wikipedia, the free encyclopedia, Oct. 9, 2010, XP002680035.
J. Sagripanti, et al., "Virus Inactivation by Copper or Iron Ions Alone and in the Presence of Peroxide", Applied and Environmental Microbiology, vol. 59, No. 12, pp. 4374-4376, Dec. 1993.
"Quaternary ammonium cation", Wikipedia.org, Apr. 14, 2016.
WPI Abstract Accession No. 1995-280817.
WPI Abstract Accession No. 1992-410101.

*Primary Examiner* — Susan Tran
(74) *Attorney, Agent, or Firm* — Norris McLaughlin & Marcus PA

(57) ABSTRACT

Compositions which impart a microbicidal benefit to treated surfaces which compositions comprise (or in certain preferred embodiments may consist essentially of, or may consist of): a zinc ion source material which releases zinc ions into the treatment composition, preferably a source of $Zn^{++}$ ions; preferably at least from about 20% wt. of at least one alcohol, which is preferably a lower alkyl monohydric alcohol and water, optionally one or more further surfactants, further optionally one or more constituents which impart one or more advantageous technical or aesthetic benefits to the compositions, including one or more detersive surfactants; and water, wherein the composition has a pH of at least 4, preferably at least 5, wherein the surface treatment compositions, exhibit a microbicidal or germicidal or antimicrobial effect on treated inanimate surfaces, characterized in exhibiting a microbicidal benefit when tested against one or more challenge microorganisms, according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces, or European Standard Surface Test, EN13697, or AOAC Germicidal Spray Products as Disinfectant Test Method, AOAC Index, $17^{th}$ Ed. (2000), preferably against poliovirus type 1 (Sabin) ("PV1").

11 Claims, No Drawings

(56) References Cited

U.S. PATENT DOCUMENTS

| | | | |
|---|---|---|---|
| 4,800,235 | A | 1/1989 | La Marre et al. |
| 4,952,398 | A | 8/1990 | Tapin |
| RE33,465 | E | 11/1990 | Eby, III |
| 4,992,212 | A | 2/1991 | Corring et al. |
| 5,043,357 | A | 8/1991 | Hoeffler et al. |
| 5,064,635 | A | 11/1991 | Casey |
| 5,174,990 | A | 12/1992 | Douglas |
| 5,180,749 | A | 1/1993 | Cusack |
| 5,208,031 | A | 5/1993 | Kelly |
| 5,227,156 | A | 7/1993 | Wiese |
| 5,348,731 | A | 9/1994 | Patti et al. |
| 5,358,979 | A | 10/1994 | van Hoboken et al. |
| 5,364,649 | A | 11/1994 | Rossmoore et al. |
| 5,373,025 | A | 12/1994 | Gay |
| 5,403,587 | A | 4/1995 | McCue et al. |
| 5,429,819 | A | 7/1995 | Oka et al. |
| 5,645,846 | A | 7/1997 | Oka et al. |
| 5,668,097 | A | 9/1997 | Trinh et al. |
| 5,670,475 | A | 9/1997 | Trinh et al. |
| 5,696,169 | A | 12/1997 | Otsu et al. |
| 5,728,404 | A | 3/1998 | von Rheinbaben et al. |
| 5,731,282 | A | 3/1998 | Duquesne |
| 5,780,064 | A | 7/1998 | Meisters et al. |
| 5,783,544 | A | 7/1998 | Trinh et al. |
| 5,798,121 | A | 8/1998 | Cauwet et al. |
| 5,827,511 | A | 10/1998 | Campbell et al. |
| 5,837,664 | A | 11/1998 | Black |
| 5,859,064 | A | 1/1999 | Cronce et al. |
| 5,908,854 | A | 6/1999 | McCue et al. |
| 5,939,060 | A | 8/1999 | Trinh et al. |
| 5,948,741 | A | 9/1999 | Ochomogo et al. |
| 5,948,742 | A | 9/1999 | Chang et al. |
| 5,968,539 | A | 10/1999 | Beerse et al. |
| 6,022,545 | A | 2/2000 | Schmittmann et al. |
| 6,046,146 | A | 4/2000 | Erilli |
| 6,077,318 | A | 6/2000 | Trinh et al. |
| 6,080,387 | A | 6/2000 | Zhou et al. |
| 6,106,851 | A | 8/2000 | Beerse et al. |
| 6,107,261 | A | 8/2000 | Taylor et al. |
| 6,113,933 | A | 9/2000 | Beerse et al. |
| 6,136,771 | A | 10/2000 | Taylor et al. |
| 6,136,776 | A | 10/2000 | Dickler et al. |
| 6,183,757 | B1 | 2/2001 | Beerse et al. |
| 6,183,763 | B1 | 2/2001 | Beerse et al. |
| 6,190,675 | B1 | 2/2001 | Beerse et al. |
| 6,190,764 | B1 | 2/2001 | Shi et al. |
| 6,197,315 | B1 | 3/2001 | Beerse et al. |
| 6,214,784 | B1 | 4/2001 | Robbins et al. |
| 6,239,096 | B1 | 5/2001 | Blum et al. |
| 6,242,009 | B1 | 6/2001 | Batarseh et al. |
| 6,245,728 | B1 | 6/2001 | Robbins et al. |
| 6,248,135 | B1 | 6/2001 | Trinh et al. |
| 6,258,368 | B1 | 7/2001 | Beerse et al. |
| 6,268,327 | B1 | 7/2001 | Lu et al. |
| 6,277,805 | B1 | 8/2001 | Kupneski |
| 6,294,186 | B1 | 9/2001 | Beerse et al. |
| 6,339,056 | B1 | 1/2002 | Like |
| 6,344,218 | B1 | 2/2002 | Dodd et al. |
| 6,346,281 | B1 | 2/2002 | DeAth et al. |
| 6,376,448 | B1 | 4/2002 | Colurciello, Jr. et al. |
| 6,387,874 | B1 | 5/2002 | Schalitz et al. |
| 6,444,707 | B1 | 9/2002 | Lampe et al. |
| 6,451,065 | B2 | 9/2002 | Trinh et al. |
| 6,468,953 | B1 | 10/2002 | Hitchems et al. |
| 6,482,392 | B1 | 11/2002 | Zhou et al. |
| 6,482,788 | B1 | 11/2002 | Arvanitidou |
| 6,492,313 | B1 | 12/2002 | Connors et al. |
| 6,495,500 | B1 | 12/2002 | Connors et al. |
| 6,498,137 | B1 | 12/2002 | Schalitz et al. |
| 6,551,553 | B1 | 4/2003 | von Rheinbaben et al. |
| 6,583,181 | B1 | 6/2003 | Chiang et al. |
| 6,610,639 | B1 | 8/2003 | Arvanitidou et al. |
| 6,617,296 | B1 | 9/2003 | Connors et al. |
| 6,635,609 | B2 | 10/2003 | Sutton |
| 6,693,070 | B1 | 2/2004 | Cheung et al. |
| 6,762,157 | B1 | 7/2004 | Babinski et al. |
| 6,793,914 | B2 | 9/2004 | Clarkson et al. |
| 6,875,733 | B1 | 4/2005 | Wojtczak et al. |
| 7,026,308 | B1 | 4/2006 | Gavin et al. |
| 7,060,302 | B1 | 6/2006 | Hickok |
| 7,087,567 | B2 | 8/2006 | Connors et al. |
| 7,163,709 | B2 | 1/2007 | Cook et al. |
| 7,182,537 | B2 | 2/2007 | Policicchio et al. |
| 7,182,941 | B2 | 2/2007 | Trinh et al. |
| 7,238,654 | B2 | 7/2007 | Hodge et al. |
| 7,455,851 | B1 | 11/2008 | Nelson et al. |
| 7,591,840 | B2 | 9/2009 | Suddaby |
| 7,625,855 | B2 | 12/2009 | Gonzalez |
| 7,629,386 | B2 | 12/2009 | Salamone |
| 7,645,746 | B1 | 1/2010 | Trinh et al. |
| 7,879,365 | B2 | 2/2011 | Modak |
| 7,915,210 | B2 | 3/2011 | Bennett et al. |
| 7,951,761 | B2 | 5/2011 | Gonzalez |
| 7,951,840 | B2 | 5/2011 | Modak |
| 7,956,024 | B2 | 6/2011 | Gonzalez |
| 8,877,698 | B2 | 11/2014 | Bennett et al. |
| 2001/0044392 | A1 | 11/2001 | Trinh et al. |
| 2001/0049347 | A1 | 12/2001 | Robbins et al. |
| 2002/0022660 | A1 | 2/2002 | Jampani et al. |
| 2002/0045667 | A1 | 4/2002 | Baker et al. |
| 2002/0057988 | A1 | 5/2002 | Diaz |
| 2002/0119207 | A1 | 8/2002 | Baker, Jr. et al. |
| 2002/0155969 | A1 | 10/2002 | Rees et al. |
| 2002/0183233 | A1 | 12/2002 | Mitra et al. |
| 2003/0013769 | A1 | 1/2003 | Mukkamala et al. |
| 2003/0032573 | A1 | 2/2003 | Tanner et al. |
| 2003/0100465 | A1 | 5/2003 | Kilkenny et al. |
| 2003/0148917 | A1 | 8/2003 | Mitra et al. |
| 2003/0153478 | A1 | 8/2003 | Sutton |
| 2003/0211066 | A1 | 11/2003 | Scholz et al. |
| 2003/0215418 | A1 | 11/2003 | Asmus et al. |
| 2003/0216273 | A1 | 11/2003 | Mitra et al. |
| 2004/0033916 | A1 | 2/2004 | Kuzmin et al. |
| 2004/0058878 | A1 | 3/2004 | Walker et al. |
| 2004/0071653 | A1 | 4/2004 | Bratescu et al. |
| 2004/0106533 | A1 | 6/2004 | Mitra et al. |
| 2004/0110841 | A1 | 6/2004 | Kite et al. |
| 2004/0171509 | A1 | 9/2004 | Fox et al. |
| 2004/0204331 | A1 | 10/2004 | Connors et al. |
| 2004/0209792 | A1 | 10/2004 | Mitra et al. |
| 2004/0213750 | A1 | 10/2004 | Bennett et al. |
| 2004/0214785 | A1 | 10/2004 | Dees et al. |
| 2004/0259951 | A1 | 12/2004 | Clarkson et al. |
| 2005/0008576 | A1 | 1/2005 | Makansi |
| 2005/0009722 | A1 | 1/2005 | Gonzalez |
| 2005/0013836 | A1 | 1/2005 | Raad |
| 2005/0015357 | A1 | 1/2005 | Shahidi |
| 2005/0019431 | A1 | 1/2005 | Modak et al. |
| 2005/0079146 | A1 | 4/2005 | Kuzmin et al. |
| 2005/0089496 | A1 | 4/2005 | Lichtenberg et al. |
| 2005/0129766 | A1 | 6/2005 | Bringley et al. |
| 2005/0164913 | A1 | 7/2005 | Polyakov et al. |
| 2005/0239675 | A1 | 10/2005 | Makansi |
| 2005/0261148 | A1 | 11/2005 | Xia et al. |
| 2006/0047006 | A1 | 3/2006 | Salamone et al. |
| 2006/0177519 | A1 | 8/2006 | Hartfeldt et al. |
| 2006/0178431 | A1 | 8/2006 | Hartfeldt et al. |
| 2006/0189483 | A1 | 8/2006 | Hickok |
| 2006/0233886 | A1 | 10/2006 | Kielbania et al. |
| 2006/0264349 | A1 | 11/2006 | Connors et al. |
| 2006/0281663 | A1 | 12/2006 | Asmus |
| 2007/0020140 | A1 | 1/2007 | Buhr et al. |
| 2007/0134136 | A1 | 6/2007 | Polyakov et al. |
| 2007/0190177 | A1 | 8/2007 | Kling et al. |
| 2007/0297990 | A1 | 12/2007 | Shah et al. |
| 2008/0045491 | A1 | 2/2008 | Fitchmun |
| 2008/0118575 | A1 | 5/2008 | Ashmore et al. |
| 2008/0138438 | A1 | 6/2008 | Taylor et al. |
| 2008/0254141 | A1 | 10/2008 | Hwu et al. |
| 2008/0292676 | A1 | 11/2008 | Crudden |
| 2008/0292721 | A1 | 11/2008 | Crudden |
| 2008/0292723 | A1 | 11/2008 | Crudden |
| 2008/0299222 | A1 | 12/2008 | Crudden |
| 2009/0018213 | A1 | 1/2009 | Snyder et al. |

(56) References Cited

U.S. PATENT DOCUMENTS

| | | | | |
|---|---|---|---|---|
| 2009/0047364 | A1 | 2/2009 | Crudden | |
| 2009/0053323 | A1 | 2/2009 | Tichy et al. | |
| 2009/0074881 | A1 | 3/2009 | Kielbania | |
| 2009/0136581 | A1 | 5/2009 | Gutierrez et al. | |
| 2009/0214606 | A1 | 8/2009 | Bujard et al. | |
| 2009/0226494 | A1 | 9/2009 | Hickok | |
| 2009/0246292 | A1 | 10/2009 | Seville et al. | |
| 2009/0304813 | A1 | 12/2009 | Hickok | |
| 2010/0015245 | A1 | 1/2010 | Harrison et al. | |
| 2010/0021562 | A1 | 1/2010 | Chowhan et al. | |
| 2010/0041580 | A1 | 2/2010 | Gonzalez | |
| 2010/0041582 | A1 | 2/2010 | Gonzalez | |
| 2010/0098777 | A1 | 4/2010 | Gould et al. | |
| 2010/0132741 | A1 | 6/2010 | Frey et al. | |
| 2010/0151046 | A1 | 6/2010 | Okamoto et al. | |
| 2010/0187263 | A1 | 7/2010 | Lestage et al. | |
| 2010/0189611 | A1 | 7/2010 | Lestage et al. | |
| 2010/0189809 | A1 | 7/2010 | Lestage et al. | |
| 2010/0209460 | A1 | 8/2010 | Pietsch | |
| 2010/0233098 | A1 | 9/2010 | Bennett et al. | |
| 2014/0127141 | A1 | 5/2014 | Ijaz et al. | |
| 2014/0134269 | A1 | 5/2014 | Ijaz et al. | |
| 2014/0140935 | A1 | 5/2014 | Ijaz et al. | |
| 2014/0147513 | A1 | 5/2014 | Ijaz et al. | |
| 2014/0161905 | A1 * | 6/2014 | Ijaz | A01N 31/02 424/638 |
| 2014/0212361 | A1 | 7/2014 | Ijaz et al. | |
| 2015/0189888 | A1 | 7/2015 | Ijaz et al. | |
| 2015/0237867 | A1 | 8/2015 | Ijaz et al. | |
| 2015/0250183 | A1 | 9/2015 | Apollo et al. | |
| 2015/0290102 | A1 | 10/2015 | Cozean et al. | |

FOREIGN PATENT DOCUMENTS

| | | | | |
|---|---|---|---|---|
| EP | 0414309 | A1 | 8/1990 | |
| EP | 0689767 | A2 | 6/1995 | |
| EP | 0848907 | A1 | 12/1997 | |
| EP | 1767495 | A1 | 6/2006 | |
| EP | 2135507 | A1 | 12/2009 | |
| JP | 04305505 | A | 10/1992 | |
| JP | 07179318 | A | 7/1995 | |
| JP | WO 0228187 | A1 * | 4/2002 | A01N 59/16 |
| WO | 0005330 | A1 | 2/2000 | |
| WO | 0030601 | A1 | 6/2000 | |
| WO | 02065838 | A1 | 8/2002 | |
| WO | 03073857 | A2 | 9/2003 | |
| WO | 03073858 | A2 | 9/2003 | |
| WO | 03075664 | A1 | 9/2003 | |
| WO | 2008154395 | A1 | 12/2008 | |
| WO | 2009130608 | A2 | 10/2009 | |
| WO | 2012136968 | A1 | 10/2012 | |
| WO | 2012164251 | A1 | 12/2012 | |
| WO | 2012164252 | A1 | 12/2012 | |
| WO | 2012164253 | A1 | 12/2012 | |
| WO | 2012164254 | A1 | 12/2012 | |
| WO | 2012164255 | A1 | 12/2012 | |
| WO | 2013142474 | A1 | 9/2013 | |
| WO | 2014006380 | A1 | 1/2014 | |
| WO | 2014006381 | A1 | 1/2014 | |
| WO | 2014006383 | A1 | 1/2014 | |

* cited by examiner

AQUEOUS ALCOHOLIC MICROBICIDAL COMPOSITIONS COMPRISING ZINC IONS

This is an application filed under 35 USC 371 of PCT/GB2013/051724, which in turn claims priority to patent applications UK 1211701.6 filed 02 Jul 2012 and U.S. Pat. No. 61/731,940 filed Nov. 30, 2012.

The present invention relates to aqueous alcoholic compositions which comprise zinc ions which compositions exhibit a microbicidal benefit when applied to inanimate surfaces. These compositions provide a surprisingly high degree of microbicidal activity against various undesirable microorganisms (sometimes referred to as 'pathogens') including various bacteria, mycobacteria, viruses, and fungi.

While ethanol and other monohydric alcohols are known to the art as having a beneficial microbicidal benefit, at the same time it is a volatile organic compound ("VOC") and there is a substantial interest in regulating the use of ethanol (as well as other volatile organic compounds) in products wherein the ethanol or other VOC is exposed to the environment. Such regulatory interests are however completely contrary to the technical benefits provided by ethanol and other monohydric alcohols. Ethanol in particular is very effective microbicidal agent, as increased levels of ethanol in a composition have long been known to exhibit increased microbicidal benefits against undesirable microorganisms.

The technical art has proposed several compositions which are lauded to provide some degree of microbicidal/germicidal/antimicrobial efficacy, at the same time to comprise reduced amounts of ethanol and other monohydric alcohols while still providing an appreciable microbicidal benefit. However, these compositions are not wholly successful in providing a microbicidal/germicidal/antimicrobial benefit against a broad range of undesirable microorganisms, and in particular in providing effective microbicidal benefit against particularly difficult to eradicate microorganisms including non-enveloped viruses, and in particular Poliovirus (e.g., poliovirus type 1 (Sabin). As is recognized in the art, demonstrated eradication of poliovirus is highly advantageous as such compositions would not only be effective in controlling this dangerous microorganism but at the same time such a high level of efficacy would also be recognized as having a high degree of relatively easier to eradicate microorganisms including but not limited to bacteria, mycobacteria, other non-enveloped and enveloped virus strains including and in many cases, fungi.

The prior art discloses various compositions which are cited to provide a microbicidal effect. For example, in U.S. Pat. No. 5,180,749 are described largely aqueous compositions comprising about 65-88% wt. water and which include as further essential constituents both about 10-30% wt. ethanol with about 2-5% wt. benzyl alcohol. However, the use of water soluble metal salts is not disclosed nor is the pH of the compositions disclosed. The compositions were tested against *Staphylococcus aureus, Salmonella choleraesuis, Pseudomonas aeruginosa*, rhinovirus type 39, herpes simplex 1, herpes simplex 2, adenovirus type 2, respiratory syncytial, influenza A2, influenza B, human rotavirus, *Mycobacterium tuberculosis* var. *bovis*, as well as fungi of types *Aspergillus niger* and *Trichopython mentgrophytes*. In that patent, when contrasting the data from Table B to the data from Table A, the necessary inclusion of benzyl alcohol in conjunction with ethanol in order to achieve increased microbicidal efficacy is shown. The poor microbicidal efficacy of compositions comprising 30% wt. ethanol and water and where benzyl alcohol is absent is demonstrated on Table B.

U.S. Pat. No. 5,728,404 discloses certain virucidal disinfectant compositions which are described as including one or more C1-C4 aliphatic alcohols, 0.1-1% wt. of a hydrolized metal ion, and water. Compositions comprising ethyl alcohol and isopropyl alcohol at ratios of 8:1 to 1:1 are noted to be particularly effective and preferred. While the document alleges that the amount of the aliphatic alcohol may be in the range of 40%-90% wt., such is not demonstrated as in the only four examples provided the amount of the aliphatic alcohols are respectively 80% wt., 70% wt., 80% wt. and 80% wt. Furthermore, when formed as described in that patent document, the composition according to Example 1 exhibited a pH of 5.48, the composition of Example 2 exhibited a pH of 5.63, and the composition of Example 3 exhibited a pH of 5.63, which indicates that the foregoing compositions consistently demonstrated an acidic pH.

The treatment of biofilms by compositions which include certain heavy metals are known from US 2008/0118573. The treatment steps require that the biofilms be contacted with the said compositions for 4 hours or more. The biofilms are defined to be conglomerates of microbial organisms embedded in highly hydrated matricies of exopolymers, typically polysaccharides, and other macromolecules.

U.S. Pat. Nos. 6,034,043 and 6,017,861 disclose liquid skin cleaning compositions comprising (1) a so-called mild surfactant system, of which at least 10% wt. of which, preferably at least 25% wt. of which, is an anionic surfactant, (2) 0.1-10% wt. of a polyvalent cation or cations selected from zinc, copper, tin, aluminum, cobalt, nickel, chromium, titanium, and/or manganese and mixtures thereof, and (3) 1-99% wt. water wherein the cations provide antimicrobial activity. The patent suggests that antimicrobial activity of the liquid skin cleaning compositions was due to the combination of the mild surfactant system with the polyvalent cation or cations which in combination, provided an antimicrobial benefit whereas the polyvalent cation or cations themselves did not. None of the demonstrated compositions include lower alkyl monohydric alcohols.

U.S. Pat. No. 6,344,218 discloses topical sanitizing gel compositions which include an odor absorber, which may be a water soluble salt such as a water soluble copper salt or water soluble zinc salt, from 40-90% wt. of an alcohol as well as an antimicrobial agent which may be a quaternary ammonium chloride. The reference states that when zinc salts are used, the pH is suitable adjusted to less than about 7, preferably less than about 6 and more preferably to less than about 5.

U.S. Pat. No. 7,871,649 discloses antimicrobially active gels, creams, ointments, lotions and soaps whose antimicrobial activity is enhanced by the inclusion of quaternary ammonium compounds and essential oils and/or one or more individual constituents thereof. These compositions are for topical application to the skin or various mucous membranes of the body. In preferred embodiments the compositions comprise 10-90% w/w alcohol, 15-70% w/w water, 0.05-3% w/w thickeners and/or gelling agents, and 0.1-3% w/w of emollients. The reference discloses that zinc salts may be present to reduce skin irritation of the gels. No mention of any antimicrobial efficacy against poliovirus is disclosed.

US 2004/0213750 discloses aqueous alcoholic compositions which comprise 40% wt.-70% wt. of a lower alkanol, optionally a quaternary ammonium cationic compound which itself provides germicidal properties, water and a pH adjusting agent to provide a final pH of between 7 and 13. The compositions are shown to be effective against various microorganisms including gram-positive and gram-negative types of pathogenic bacteria, as well as poliovirus type 1 at a 10 minute contact time. The reference makes no mention of the use of zinc ions in the compositions.

Further known to the art are the compositions disclosed in US 2007/0184013 which compositions are cited to be effective against non-enveloped virus particles. The compositions comprise a $C_1$-$C_6$ alcohol and an efficacy-enhancing amount of one or more of: cationic oligomers and polymers, proton donors, chaotropic agents, and mixtures thereof with the proviso that when the compositions include a proton donor, a cationic oligomer or polymer is also present. The cationic oligomers and polymers disclosed are defined to include cationic polyalkylene imines, cationic ethoxy polyalkylene imines, cationic poly[N-[3-(dialkylammonio)alkyl]N'[3-(alkyleneoxyalkylene dialkylammonio)alkyl]urea dichloride], vinyl caprolactam/VP/dialkylaminoalkyl alkylate copolymers and polyquaternium copolymers. The example compositions disclosed in the reference demonstrate compositions having 62% and even greater amounts of the $C_1$-$C_6$ alcohol as being present.

US 2008/0045491 discloses certain surface sanitizer compositions which are recited to include 50-90% of an alcohol component, 10-50% of water, an acid component to maintain the pH of the composition between 2-5, and 0.05-5%, of a multivalent cation constituent. The multivalent cation constituent may be a one of a selected list of polymers, a metal ion, or a metal compound. The compositions may optionally include one or more further constituents, including oxidative agents, plant derived alkenes or essential oils, emollients, humectants, lubricants and one or more antimicrobial compounds, e.g., quaternary ammonium compounds. A single example of US 2008/0045491 demonstrates that a composition having 78% wt. ethanol exhibits efficacy against *Candida albicans, Aspergillus niger, Escherichia coli, Pseudomonas aeruginosa, Staphylococcus aureus* and Adenovirus type 5. The further examples of US 2008/0045491 are not disclosed to have been tested against any microorganisms.

US 2008/0138438 discloses certain antimicrobial compositions having antiviral and antibacterial efficacy which include a divalent zinc salt, optionally a disinfecting alcohol, optionally an antimicrobial agent, and optionally an organic acid. The compositions exhibit a pH of about 5 or less, preferably a pH of less than 4.5 and especially preferably a pH in the range of about 2.5 to about 4.5.

US 2010/0151046 discloses certain disinfectant compositions which comprise ethanol, a zinc containing compound which releases zinc ions in solution, and a combination of lactic acid with citric acid. The composition expressly excludes further antimicrobial disinfecting agents.

US 2010/0233098 discloses methods and compositions for disinfecting hard surfaces which are aqueous compositions which comprise 40% wt.-70% wt. of an alcohol constituent selected from the group consisting of methanol, ethanol, n-propanol, isopropanol, n-butanol, benzyl alcohol, and mixtures thereof and a pH in the range of from about 7.0-14.0. The compositions may include further optional constituents, including ancillary antimicrobial agents, and surfactants. The use of water soluble metal salts is not disclosed.

Notwithstanding these various known art compositions, there is still an urgent need in the art to produce treatment compositions, particularly those adapted for the control or eradication of undesired microorganisms where such treatment compositions comprise reduced amounts of VOC, and in particular aliphatic alcohols which provide a microbicidal effect such as ethanol, yet which compositions are highly effective against particularly difficult to eradicate undesired microorganisms, especially poliovirus, particularly where the treatment compositions are applied to an inanimate surface.

In a broad aspect, the compositions of the present invention are generally directed to liquid inanimate surface treatment compositions which impart an antimicrobial or microbicidal benefit to treated surfaces which compositions comprise (or in certain preferred embodiments may consist essentially of, or may consist of): water, a zinc ion source material which releases zinc ions into the treatment composition (preferably Zn++ ions), and at least one alcohol which independently of other constituents present exhibits a microbicidal effect, and wherein the compositions are at a pH such that they exhibit a microbicidal effect on treated surfaces. In certain embodiments, the compositions further additionally comprise at least one quaternary ammonium compound which provides a microbicidal benefit. In still further embodiments, the compositions further additionally comprise at least one detersive surfactant, which in certain preferred embodiments is preferably at least one nonionic surfactant. These aforesaid compositions optionally include one or more further constituents which impart one or more advantageous technical or aesthetic benefits to the compositions. The compositions are at a pH such that the liquid inanimate surface treatment compositions, exhibit a microbicidal or antimicrobial effect on inanimate treated surfaces. Preferably these treatment compositions are characterized in exhibiting a microbicidal benefit when tested against one or more challenge organisms according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces, or European Standard Surface Test, EN13697, or AOAC Germicidal Spray Products as Disinfectant Test Method, AOAC Index, $17^{th}$ Ed. (2000) against one or more challenge microorganisms. Preferably the compositions are liquid, or sprayable liquid compositions (e.g. pumpable but are not aerosol compositions) and exhibit a viscosity of not more than about 100 cPs, preferably 50 cPs, more preferably about 10 cPs at 20° C. when tested according to conventional quantitative methods (e.g., Brookfield Viscometer) and are pourable, readily flowable liquids. Such may be provided in any other apparatus or device wherein the liquid composition may be poured or sprayed onto a surface. The inventive compositions provide a high degree of microbicidal activity against various undesirable microorganisms (sometimes referred to as 'pathogens') including various bacteria, mycobacteria, viruses, and fungi.

Within this broad aspect, the present inventors have surprisingly observed that there may be formed compositions which exhibit a synergistic improvement in microbicidal effect when there are present in the aqueous alcoholic liquid compositions at specific pH ranges, especially preferably at alkaline pH ranges, small but effective amounts of a material which provides a zinc ion to the aqueous alcoholic liquid compositions and (optionally but in most cases), especially wherein at least one further surfactant (preferably at least one nonionic surfactant) is also present. Such an effect is surprising, and also particularly technically advantageous, as improved microbicidal efficacy has been observed against particularly difficult to control (or eradicate) microorganisms and in particular poliovirus, while at the same time achieving these effects in aqueous alcoholic liquid compositions having a reduced VOC content. As is known to the art, non-enveloped viruses including poliovirus is particularly difficult to control or eradicate, and demonstrated microbicidal efficacy against poliovirus is expected to be indicative of microbicidal efficacy against other non-enveloped viruses and microorganisms which are less difficult to control or eradicate.

In a first aspect, the present invention provides liquid, inanimate surface treatment compositions which impart a microbicidal benefit to treated surfaces which compositions comprise (or in certain preferred embodiments may consist essentially of, or may consist of) the following constituents:

a zinc ion source material which releases zinc ions into the treatment composition, preferably a source of $Zn^{++}$ ions;

at least one lower alkyl aliphatic monohydric alcohol;

water;

optionally, one or more further constituents which impart one or more advantageous technical or aesthetic benefits to the compositions, including one or more detersive surfactants;

wherein the composition has a pH of at least about 6, wherein the surface treatment compositions are characterized in exhibiting a microbicidal benefit when tested against one or more challenge microorganisms, especially preferably against poliovirus type 1 (Sabin) ("PV1") according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces, or European Standard Surface Test, EN13697, or AOAC Germicidal Spray Products as Disinfectant Test Method, AOAC Index, $17^{th}$ Ed. (2000).

In a second aspect the present invention provides liquid, inanimate surface treatment compositions which impart a microbicidal benefit to such treated surfaces which compositions comprise (or in certain preferred embodiments may consist essentially of, or may consist of) as constituents:

a zinc ion source material which releases zinc ions into the treatment composition, preferably a source of $Zn^{++}$ ions;

at least one lower alkyl aliphatic monohydric alcohol;

at least one quaternary ammonium surfactant compound which provides a microbicidal benefit;

water;

optionally, one or more further constituents which impart one or more advantageous technical or aesthetic benefits to the compositions, including one or more detersive surfactants;

wherein the composition has a pH of at least about 6, wherein the surface treatment compositions are characterized in exhibiting a microbicidal benefit when tested against one or more challenge microorganisms, especially preferably against poliovirus type 1 (Sabin) ("PV1"), according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces, or European Standard Surface Test, EN13697, or AOAC Germicidal Spray Products as Disinfectant Test Method, AOAC Index, $17^{th}$ Ed. (2000).

In a third aspect the present invention provides liquid, inanimate surface treatment compositions which impart a microbicidal benefit to such treated surfaces which compositions comprise (or in certain preferred embodiments may consist essentially of, or may consist of) the constituents:

a zinc ion source material which releases zinc ions into the treatment composition, preferably a source of $Zn^{++}$ ions;

at least one lower alkyl aliphatic monohydric alcohol;

at least one further detersive surfactant, other than at least one quaternary ammonium compound which provides a microbicidal benefit, as compared to where such at least one such further detersive surfactant is absent, which at least one further detersive surfactant is preferably at least one nonionic surfactant:

water;

optionally, one or more further constituents which impart one or more advantageous technical or aesthetic benefits to the compositions, including one or more detersive surfactants;

wherein the composition has a pH of at least about 6, wherein the treatment compositions are characterized in exhibiting a microbicidal benefit, especially preferably against poliovirus type 1 (Sabin) ("PV1"), when tested according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces, or European Standard Surface Test. EN13697, or AOAC Germicidal Spray Products as Disinfectant Test Method, AOAC Index, $17^{th}$ Ed. (2000) against one or more challenge microorganisms.

In a fourth aspect the present invention provides liquid, inanimate surface treatment compositions which impart a microbicidal benefit to such treated surfaces which compositions comprise (or in certain preferred embodiments may consist essentially of, or may consist of) the constituents:

a zinc ion source material which releases zinc ions into the treatment composition, preferably a source of $Zn^{++}$ ions:

at least one lower alkyl aliphatic monohydric alcohol;

at least one quaternary ammonium surfactant compound which provides a microbicidal benefit;

at least one further detersive surfactant, other than at least one quaternary ammonium compound which provides a microbicidal benefit, as compared to where such at least one such further detersive surfactant is absent, which at least one further detersive surfactant is preferably at least one nonionic surfactant;

water;

optionally, one or more further constituents which impart one or more advantageous technical or aesthetic benefits to the compositions, including one or more detersive surfactants;

wherein the composition has a pH of at least about 6, wherein the surface treatment compositions are characterized in exhibiting a microbicidal benefit, especially preferably against poliovinrus type 1 (Sabin) ("PV1"), when tested according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces, or European Standard Surface Test, EN13697, or AOAC Germicidal Spray Products as Disinfectant Test Method, AOAC Index, 17th Ed. (2000) against one or more challenge microorganisms.

In a fifth aspect the present invention provides liquid, inanimate surface treatment compositions which impart a microbicidal benefit to such treated surfaces which compositions comprise (or in certain preferred embodiments may consist essentially of, or may consist of) as constituents:

a zinc source material which releases zinc ions into the treatment composition, preferably a source of Zn++ ions;

at least 35% wt. of at least one lower alkyl aliphatic monohydric alcohol, and wherein a) when compositions comprise 35% wt. to <45% wt. of at least one lower alkyl aliphatic monohydric alcohol, the pH of the compositions are ≥9.46 and <11;

b) when compositions comprise ≥45% wt. to ≤55% wt. of at least one lower alkyl aliphatic monohydric alcohol, the pH of the compositions are ≥9.46 and <11;

at least one quaternary ammonium compound which provides a microbicidal benefit;

water;

optionally, one or more further constituents which impart one or more advantageous technical or aesthetic benefits to the compositions, including one or more detersive surfactants;

and, wherein the surface treatment compositions are characterized in exhibiting at least a 3 log 10 result when tested against poliovirus type 1 (Sabin) ("PV1") tested according to one or more of the following standardized test protocols: ASTM E1052 Standard Test Method for Efficacy of Antimicrobial Agents against Viruses in Suspension, or, ASTM E1053 Standard Test Method to Assess Virucidal Activity of Chemicals Intended for Disinfection of Inanimate, Nonporous Environmental Surfaces.

In the foregoing, preferably at least one detersive surfactant is also present, preferably a nonionic surfactant, as a further essential constituent.

In a further aspect the present invention provides surface treatment compositions according to any foregoing aspects of the invention which compositions exhibit a pH of at least at least 6, yet more preferably at least 7.

In a further aspect the present invention provides surface treatment compositions according to any foregoing aspects of the invention which compositions concurrently satisfy at least one of the following Conditions A, B, C, D, E, F, G, H, I, J, K, L. M, and N:

| Condition | pH or pH range | % wt. of at least one lower alkyl aliphatic monohydric alcohol | $\log_{10}$ reduction of poliovirus type 1 (Sabin) ("PV1") when tested according to the standardized test protocol: ASTME E1052 |
|---|---|---|---|
| A | ≥8.5 | ≥40 and ≤45.2 | at least 1.5 |
| B | ≥8.5 to <9 | ≥40 and ≤45.2 | at least 2.5 |
| C | ≥9 to <9.5 | ≥20 and ≤70.2 | at least 0.5 |
| D | ≥9.5 to <10 | ≥35 and ≤50 | at least 3.3 |
| E | >10 to <10.5 | ≥40 and ≤50 | at least 5.0 |
| F | ≥10.5 to <11 | ≥35 and ≤50 | at least 5.0 |
| G | ≥11 | ≥35 and ≤50 | at least 5.0 |

| Condition | pH or pH range | % wt. of at least one lower alkyl aliphatic monohydric alcohol | $\log_{10}$ reduction of poliovirus type 1 (Sabin) ("PV1") when tested according to the standardized test protocol: ASTM E1053 |
|---|---|---|---|
| H | >8.5 | ≥40 and ≤45.2 | — |
| I | ≥8.5 to <9 | ≥40 and ≤45.2 | at least 1.67 |
| J | ≥9 to <9.5 | ≥20 and ≤70.2 | at least 2 |
| K | ≥9.5 to <10 | ≥35 and ≤50 | at least 1.67 |
| L | ≥10 to <10.5 | ≥40 and ≤50 | at least 3.3 |
| M | ≥10.5 to <11 | ≥35 and ≤50 | at least 3.5 |
| N | ≥11 | ≥35 and ≤50 | at least 4.27 |

In a further aspect the present invention provides surface treatment compositions according to any foregoing aspects of the invention which compositions concurrently satisfy at least one of the following Conditions O, P, Q, R, S, T, U, and V:

| Condition | % wt. of at least one lower alkyl aliphatic monohydric alcohol | pH or pH range | $\log_{10}$ reduction of poliovirus type 1 (Sabin) ("PV1") when tested according to the standardized test protocol: ASTM E1052 |
|---|---|---|---|
| O | ≥20 and <40 | ≥9.03 and ≤10.76 | at least 2.0 |
| P | ≥40 and <45 | ≥7.92 and ≤11.51 | at least 2.0 |
| Q | ≥45 and <50 | ≥6.07 and ≤11.5 | at least 1.5 |
| R | ≥50 | ≥9.03 and ≤9.2 | at least 4.17 |

| Condition | % wt. of at least one lower alkyl aliphatic monohydric alcohol | pH or pH range | $\log_{10}$ reduction of poliovirus type 1 (Sabin) ("PV1") when tested according to the standardized test protocol: ASTM E1053 |
|---|---|---|---|
| S | ≥20 and <40 | ≥9.03 and ≤10.76 | — |
| T | ≥40 and <45 | ≥7.92 and ≤11.51 | at least 1.67 |
| U | ≥45 and <50 | ≥6.07 and ≤11.5 | at least 1.67 |
| V | ≥50 | ≥9.03 and ≤9.2 | at least — |

In a still further aspect the present invention provides a method of controlling the incidence of undesired microorganisms on an inanimate surface, the method comprising the step of: contacting the inanimate surface which is in need of treatment or upon which the presence of one or more undesirable microorganisms are suspected or are known to be present, with an effective amount of a liquid, inanimate surface treatment composition as described herein to provide a surface treatment benefit thereto, preferably to provide a microbicidal benefit to the contacted surface.

In an additional aspect the present invention provides a vendible product, as well as a method for the manufacture of such a vendible product which comprises a surface treatment composition as described herein.

These and further aspects of the invention will become more apparent from a reading of the following specification.

A first essential constituent of the invention is a zinc ion source material which provides zinc ions which are compounds, constituents or materials which are at least partially soluble in the aqueous alcoholic base of the inventive compositions Preferably such compounds, constituents or materials release zinc ions (e.g., preferably Zn++) within the inventive compositions. Such include zinc compounds having a counterion selected from acetate, acetylacetonate, bromide, bromide, citrate, chloride, formate, gluconate, glycerophosphate, iodide, lactate, nitrate, salycilate, sulfate, pyrithione and tartrate. By way of non-limiting example, such include species such as zinc acetate, zinc butyrate, zinc citrate, zinc chloride, zinc gluconate, zinc glycolate, zinc glycerate, zinc glycolate, zinc formate, zinc lactate, zinc monohydrate, zinc picolinate, zinc proprionate, zinc salycilate, zinc sulfate, zinc tartrate, and zinc undecylenate. The zinc ion source may be in a hydrated form. The zinc ion source may comprise one or more said compounds, constituents or materials. Preferred zinc ion sources include zinc salts of an organo-carboxylic acid having from about 2 to about 6 carbon atoms, such as zinc salts of acetates, glycolates, lactates, gluconate and citrates. Particularly preferred zinc ion sources are disclosed in one or more of the Examples.

The zinc ion source materials need not be fully soluble within the treatment compositions provided by the present invention and may, for example, be dispersions.

The zinc ion source material may be present in the treatment compositions in any effective amount and may provide as little as about 0.5 ppm (part per million) of the zinc ion to the composition, but advantageously is present in an amount of at least about 0.001% wt. to about 2.5% wt, preferably from about 0.01% wt to about 1% wt., and particularly preferably from about 0.01% wt. to about 0.5% wt. Alternately, the zinc ion source material may be present in the treatment compositions in a sufficient amount such that the zinc ion source material releases zinc ions, and preferably Zn++ ions, into the treatment composition so to provide between about 1 ppm to about 10,000 ppm of zinc ions, preferably to about (in order of increasing preference) 9500, 9000, 8500, 8000, 7500, 7000, 6750, 6500, 6250, 6000, 5750, 5500, 5250, 5000, 4750, 4500, 4250, 4000, 3750, 3500, 3250, 3000, 2750, 2500, 2400, 2300, 2250, 2200, 2100, 2000, 1900, 1800, 1750, 1700, 1650, 1600, 1550, 1500, 1450, 1400, 1350, 1300, 1250, 1200, 1150, 1100, 1050, 1000, 975, 950, 925, 900, 875, 850, 825, 800, 775, 750, 725, 700, 675, 650, 625, 600, 575, 550, 500, 475, 450, 425, 400, 375, 350, 325, 300, 275, 250, 225, 200, 175, 150, 125, 100, 95, 90, 85, 80, 75, 70, 65, 60, 55, 50, 45, 40, 35, 30, 25, 20, 15, 10, 9, 8, 7, 6, 5, 4, 3, 2, 1 ppm, and/or alternately any integer number value within the above range of 1-10,000 ppm of zinc ions, within the inventive compositions taught herein.

Exclusive of counterions of surfactant compounds or counterions of other materials described herein which might be present, most preferably the zinc ion source material is the sole material present in the composition which releases available metal ions to the treatment compositions taught herein. In certain preferred embodiments the zinc ion source material is the sole source of zinc ions in the compositions of the invention.

A further essential constituent of the inventive compositions is at least one lower alkyl aliphatic monohydric alcohol. Preferably this at least one lower alkyl aliphatic monohydric alcohol also exhibits a biocidal effect against microorganisms independently of the other constituents which may be present in the compositions. Exemplary and preferred are $C_1$-$C_6$ mononhydric alcohols, especially methanol, ethanol, n-propanol, isopropanol, and all isomers of butanol. Of these, $C_1$-$C_4$ monohydric alcohols, and especially $C_1$-$C_3$ mononhydric alcohols are preferred, especially ethanol. A single such alcohol, or mixture of two or more such alcohols may be present. In certain embodiments when a plurality of alcohols are present, ethanol is the predominant alcohol present, and especially preferably comprises at least 50.1% wt., and especially preferably and in order of increasing preference, at least 51%, 55%, 60%, 65%, 70%, 75%, 80%, 85%, 90%, 92%, 95%, 97%, 98%, 99%, 99.5% and 100% by weight of the at least one lower alkyl aliphatic monohydric alcohol present.

While the amount of the at least one lower alkyl aliphatic monohydric alcohol may be present in any amount, including amounts of as little as about 1% wt., in certain preferred embodiments the at least one lower alkyl aliphatic monohydric alcohol comprises at least 20% wt of the treatment composition of which it forms a part. Preferably the at least one lower alkyl aliphatic monohydric alcohol constituent is present in the treatment composition in an amount of as little as about 0.1% wt. but preferably is present in an amount of at least about (in order of increasing preference: 0.5%, 1%, 2%, 3%, 4%, 5%, 6%, 7%, 8%, 9%, 10%, 11%, 12%, 13%, 14%, 15%, 16%, 17%, 18%, 19%, 20%, 20.5%, 21%, 21.5%, 22%, 22.5%, 23%, 23.5%, 24%, 24.5%, 25%, 25.5%, 26%, 26.5%, 27%, 27.5% 28%, 28.5%, 29%, 29.5%, 30%, 30.5%, 31%, 31.5%, 32%, 32.5%, 33%, 33.5%, 34%, 34.5%, 35%, 35.5%, 36%, 36.5%, 37%, 37.5%, 38%, 38.5%, 39%, 39.5%, 40%, 40.5%, 41%, 41.5%, 42%, 42.5%, 43%, 43.5%, 44%, 44.5%, 45%, 45.5%, 46%, 46.5%, 47%, 47.5%, 48%, 48.5%, 49%, 49.5%, 50%, 51%, 52%, 53%, 54%, 55%, 56%, 57%, 58%, 59%, 60% 61%, 62%, 63%, 64%, 65%, 66%, 67%, 68%, 69% and 70% by weight. Concurrently and preferably the at least one lower alkyl aliphatic monohydric alcohol constituent is present in the treatment composition in an amount of up to about 99% wt., and in order of increasing preference is present in an amount up to 95%, 90%, 85%, 80%, 75%, 70%, 69%, 68%, 67%, 66%, 65%, 64%, 63%, 62%, 61%, 60%, 59%, 58%, 57%, 56%, 55%, 54%, 53%, 52%, 51%, 50%, 49.5%, 49%, 48.5%, 48%, 47.5%, 47%, 46.5%, 46%, 45.5%, 45%, 44.5% 44%, 43.5%, 43%, 42.5%, 42%, 41.5%, 41%, 40.5%, 4%, 39.5%, 39%, 38.5%, 38%, 37.5%, 37%, 36.5%, 36%, 35.5%, 35%, 34.5%, 34%, 33.5%, 33%, 32.5%, 32%, 31.5%, 31%, 30.5%, 30%, 29.5%, 29%, 28.5%, 28%, 27.5%, 27%, 26.5%, 26%, 25.5%, 25%, 24.5%, 24%, 23.5%, 23%, 22.5%, 22%, 21.5%, 21%, 20.5%, 20%, 19%, 18%, 17%, 16%, 15%, 14%, 13%, 12%, 11%, 10%, 9%, 8%, 7%, 6%, 5%, 4%, 3%, 2%, 1%, and about 0.5% by weight of the composition of which it forms a part.

In certain preferred embodiments the compositions preferably comprise from 20% wt. to 40% wt. of at least one lower alkyl aliphatic monohydric alcohol, and preferably in an amount up to but excluding 40% wt., and especially preferably where ethanol was the predominant or sole alkyl aliphatic monohydric alcohol present in the lower alkyl aliphatic monohydric alcohol constituent.

In certain preferred embodiments the compositions preferably comprise from about 40% wt. to about 50% wt., of at least one lower alkyl aliphatic monohydric alcohol, and especially preferably where ethanol was the predominant or sole alkyl aliphatic monohydric alcohol present in the lower alkyl aliphatic monohydric alcohol constituent.

Advantageously the lower alkyl aliphatic monohydric alcohol constituent exhibits a microbicidal effect against one or more pathogens even in the absence of the further constituents of the treatment compositions taught herein. For this reason, $C_1$-$C_3$ monohydric aliphatic alcohols, e.g., methanol, ethanol and the various isomers of propanol are particularly preferred whether used singly or in mixtures of two or more selected $C_1$-$C_3$ monohydric aliphatic alcohols as the sole constituents of the lower alkyl aliphatic monohydric alcohol constituent. In certain embodiments a single $C_1$-$C_3$ monohydric aliphatic alcohol is present as the second essential constituent. In certain further preferred embodiments, ethanol is the sole constituent of the lower alkyl aliphatic monohydric alcohol constituent.

As the inventive compositions are, in part, aqueous, water is added in order to provide to 100% by weight of the compositions of the invention and is thus a further essential constituent. The water may be tap water, but is preferably distilled and is most preferably deionized water. If the water is tap water, it is preferably substantially free of any undesirable impurities such as organics or inorganics, especially mineral salts which are present in hard water and which may undesirably interfere with the operation of the constituents present in the aqueous compositions according to the invention. Water may comprise as little as about 1% wt. to about 99% wt. of the compositions taught herein. Preferably water comprises at least about 10% wt. and more preferably in order of increasing preference at least about 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% by weight of the composition of which it forms a part. Preferably, water comprises up to about 99% wt, 08%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11% and about 10% wt. of the composition of which the water forms a part. Particularly preferred amounts of water are disclosed in one or more of the examples. In preferred embodiments the total amount of water and the at least one or more lower alkyl aliphatic monohydric alcohol(s) present comprise at least 80% wt, yet more preferably and in order of increasing preference comprise at least about 81%, 82%, 83%, 84%, 85%, 86%, 87%, 88%, 89%, 90%, 91%, 92%, 93%, 94%, 95%, 96%, 97%, 98%, and 99% by weight of the compositions of which they form a part.

The present inventors have found that these three essential constituents, when at a pH of 6 or greater, preferably 7 or greater, form a highly effective system which exhibits a high degree of microbicidal efficacy even in the absence of further constituents. Advantageously however this system may be supplemented by one or more further constituents.

While not wishing to be bound by the following, the present inventors have surprisingly found that by careful selection of: (1) the nature and amounts of the zinc ion source material which releases zinc ions into the treatment composition, and especially preferably wherein the zinc ion source material is a source of $Zn^{++}$ ions, (2) the at least one aliphatic monohydric alcohol which itself exhibits an independent microbicidal effect, (3) water, and (4) the pH level of the surface treatment composition, the resultant compositions provide unexpectedly excellent microbicidal efficacy against a range of undesirable microorganisms including certain viruses, bacteria and certain fungi, which has heretofore not been expected from compositions which include the reduced amounts of the alcohol constituent provided in the inventive compositions. The resultant compositions provide unexpectedly excellent microbicidal efficacy against a range of undesirable microorganisms including certain viruses, bacteria and certain fungi, which has heretofore not been expected from compositions which include the reduced amounts of the alcohol constituent provided in the inventive compositions. Such an effect has been observed even when a very limited amount of the zinc ion source material is present, and wherein the amount of the one lower alkyl aliphatic monohydric alcohol is also present in reduced amounts, e.g, in amount of between about 10% wt. to about 50% wt, or in even lesser amounts. Reference is made to the various Examples provided in this patent specification which demonstrates this effect, particularly as against comparative formulations which omit one or more of: the zinc ion source material, or the at least one alcohol. Although the literature describes the biochemical mechanisms of the separate microbicidal actives (the first, and the second essential constituents) when these microbicidal actives are used singly, surface treatment compositions as now disclosed by the inventors are believed to be unknown, particularly wherein such surface treatment compositions exhibit what is believed to be a synergistic benefit.

In a further aspect of the invention there is provided a microbicidal control system of constituents which are in and of themselves (namely, in the absence of further constituents,) effective in providing control of poliovirus independently of further and optional constituents. This microbicidal control system of constituents comprise (or consists essentially of, or consists of): water, one or more one or more $C_1$-$C_4$ aliphatic alcohols, and especially preferably wherein ethanol is the predominant or sole $C_1$-$C_4$ aliphatic alcohol present, and a zinc ion source material which is preferably a source of $Zn^{++}$ ions. The microbial control system of constituents may optionally, and in certain embodiments necessarily further include one or more of: at least one cationic quaternary ammonium compound which provides a microbicidal benefit, at least one further detersive surfactant other than the said cationic quaternary ammonium compound, which optional further detersive surfactant provides an improvement to the microbicidal efficacy of the control system, preferably against poliovirus, as compared to where such at least one such further detersive surfactant is absent, and further, a buffer or pH adjusting agent to impart an alkaline pH, preferably an alkaline pH of about 7.5 or greater. In preferred embodiments, the least one further detersive surfactant is preferably at least one nonionic surfactant. Preferably the microbicidal control system is characterized in exhibiting a microbicidal benefit when tested against one or more challenge microorganisms according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces, or European Standard Surface Test, EN1369, or AOAC Germicidal Spray Products as Disinfectant Test Method, AOAC Index, $17^{th}$ Ed. (2000), especially preferably against poliovirus type 1 (Sabin) ("PV1").

In certain preferred embodiments the microbicidal control system of constituents necessarily includes the at least one cationic quaternary ammonium compound which provides a microbicidal benefit.

In certain preferred embodiments the microbial control system of constituents necessarily includes at least one further detersive surfactant, other than a cationic quaternary ammonium compound, which further detersive surfactant provides an improvement to the control of poliovirus by the treatment composition, as compared to where such at least one such further detersive surfactant is absent, which at least one further detersive surfactant is preferably at least one nonionic surfactant.

Any of the foregoing microbicidal control systems of constituents may be included in liquid inanimate surface treatment composition which include further additional constituents and thus form a part thereof. Alternately, the foregoing microbicidal control systems of constituents may of themselves be representative of a liquid inanimate surface treatment composition. Thus, in this specification any disclosure or discussions relevant to or regarding liquid inanimate surface treatment compositions may be considered similarly applicable and relevant to the antimicrobial control systems disclosed herein.

The liquid inanimate surface treatment compositions may further optionally comprise one or more additional constituents which impart one or more advantageous technical or aesthetic benefits to the compositions.

Optionally but in many cases, the treatment compositions also comprise at least one quaternary ammonium compound which itself provides a microbicidal benefit. For the purposes of the present invention described herein, such quaternary ammonium compounds are to be understood as being outside of the scope of the defined detersive surfactants as such materials are primarily provided to impart a microbicidal effect, and not provide an appreciable detersive benefit. Any cationic surfactant which satisfies these requirements may be used and is considered to be within the scope of the present invention. Mixtures of two or more cationic surface active agents, viz., cationic surfactants may also be used. Cationic surfactants are well known, and useful cationic surfactants may be one or more of those described for example in *McCutcheon's Functional Materials, Vol.* 2, 1998*; Kirk-Othmer, Encyclopedia of Chemical Technology,* 4th Ed., Vol. 23, pp. 481-541 (1997), the contents of which are herein incorporated by reference. These are also described in the respective product specifications and literature available from the suppliers of these cationic surfactants.

Examples of preferred cationic surfactant compositions useful in the practice of the instant invention are those which provide a microbicidal or germicidal effect to the compositions, and especially preferred are quaternary ammonium compounds and salts thereof, which may be characterized by the general structural formula:

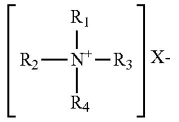

where at least one of $R_1$, $R_2$, $R_3$ and $R_4$, is a alkyl, aryl or alkylaryl substituent of from 6 to 26 carbon atoms, and the entire cation portion of the molecule has a molecular weight of at least 165. The alkyl substituents may be long-chain alkyl, long-chain alkoxyaryl, long-chain alkylaryl, halogen-substituted long-chain alkylaryl, long-chain alkylphenoxyalkyl, arylalkyl, etc. The remaining substituents on the nitrogen atoms other than the abovementioned alkyl substituents are hydrocarbons usually containing no more than 12 carbon atoms. The substituents $R_1$, $R_2$, $R_3$ and $R_4$ may be straight-chained or may be branched, but are preferably straight-chained, and may include one or more amide, ether or ester linkages. The counterion X may be any salt-forming anion which permits for the solubility of the quaternary ammonium complex within the treatment composition.

Exemplary quaternary ammonium salts within the above description include the alkyl ammonium halides such as cetyl trimethyl ammonium bromide, alkyl aryl ammonium halides such as octadecyl dimethyl benzyl ammonium bromide, N-alkyl pyridinium halides such as N-cetyl pyridinium bromide, and the like. Other suitable types of quaternary ammonium salts include those in which the molecule contains either amide, ether or ester linkages such as octyl phenoxy ethoxy ethyl dimethyl benzyl ammonium chloride, N-(laurylcocoamninoformylmethyl)-pyridinium chloride, and the like. Other very effective types of quaternary ammonium compounds which are useful as germicides include those in which the hydrophobic radical is characterized by a substituted aromatic nucleus as in the case of lauryloxyphenyltrimethyl ammonium chloride, cetylaminophenyltrimethyl ammonium methosulfate, dodecylphenyltrimethyl ammonium methosulfate, dodecylbenzyltrimethyl ammonium chloride, chlorinated dodecylbenzyltrimethyl ammonium chloride, and the like.

Preferred quaternary ammonium compounds which act as germicides and which are useful in the practice of the present invention include those which have the structural formula:

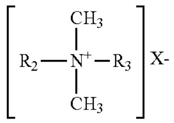

wherein $R_2$ and $R_3$ are the same or different $C_8$-$C_{12}$alkyl, or $R_2$ is $C_{12-16}$alkyl, $C_{8-18}$alkylethoxy, $C_{8-18}$alkylphenolethoxy and $R_3$ is benzyl, and X is a halide, for example chloride, bromide or iodide, a saccharinate counterion or is a methosulfate anion. The alkyl groups recited in $R_2$ and $R_3$ may be straight-chained or branched, but are preferably substantially linear.

Particularly useful quaternary ammonium compounds include compositions which include a single quaternary compound, as well as mixtures of two or more different quaternary compounds. Such useful quaternary compounds are available under the BARDAC®, BARQUAT®, HYAMINE®, LONZABAC® and ONYXIDE® trademarks, which are more fully described in, for example, *McCutchcon's Functional Materials* (Vol. 2), North American Edition, 1998, as well as the respective product literature from the suppliers identified below. Such include, for example, BARDAC® 205M which is described to be a liquid containing alkyl dimethyl benzyl ammonium chloride, octyl decyl dimethyl ammonium chloride; didecyl dimethyl ammonium chloride, and dioctyl dimethyl ammonium chloride (50% active) (also available as 80% active (BARDAC® 208M)); BARDAC® 2050 which is described to be a combination of octyl decyl dimethyl ammonium chloride/didecyl dimethyl ammonium chloride, and dioctyl dimethyl ammonium chloride (50% active) (also available as 80% active (BARDAC® 2080)); BARDAC® 2250 which is described to be didecyl dimethyl ammonium chloride (50% active); BARDAC® LF (or BARDAC® LF-80), described as being based on dioctyl dimethyl ammonium chloride (BARQUAT® MB-50, MX-50, OJ-50 (each 50% liquid) and MB-80 or MX-80 (each 80% liquid) are each described as an alkyl dimethyl benzyl ammonium chloride; BARDAC® 4250 and BARQUAT® 4250Z (each 50% active) or BARQUAT® 4280 and BARQUAT 4280Z (each 80% active) are each described as alkyl dimethyl benzyl ammonium chloride/alkyl dimethyl ethyl benzyl ammonium chloride. Also, HYAMINE® 1622, described as diisobutyl phenoxy ethoxy ethyl dimethyl benzyl ammonium chloride (50% solution); HYAMINE® 3500 (50% actives), described as alkyl dimethyl benzyl ammonium chloride (also available as 80% active (HYAMINE® 3500-80)); and HYMAINE® 2389 described as being based on methyldodecylbenzyl ammonium chloride and/or methyldodecylxylene-bis-trimethyl ammonium chloride. (BARDAC®, BARQUAT® and HYAMINE® are presently commercially available from Lonza, Inc., Fairlawn, N.J.). BTC® 50 NF (or BTC® 65 NF) is described to be alkyl dimethyl benzyl ammonium chloride (50% active); BTC® 99 is described as didecyl dimethyl ammonium chloride (50% active); BTC® 776 is described to be myrisalkonium chloride (50% active); BTC® 818 is described as being octyl decyl dimethyl ammonium chloride, didecyl dimethyl ammonium chloride, and dioctyl dimethyl ammonium chloride (50% active) (available also as 80% active (BTC® 818-80%)); BTC® 824 and BTC® 835 are each described as being of alkyl dimethyl benzyl ammonium chloride (each 50% active); BTC® 885 is described as a combination of BTC® 835 and BTC® 818 (50% active) (available also as 80% active (BTC® 888)); BTC® 1010 is described as didecyl dimethyl ammonium chloride (50% active) (also available as 80% active (BTC® 1010-80)); BTC® 2125 (or BTC® 2125 M) is described as alkyl dimethyl benzyl ammonium chloride and alkyl dimethyl ethylbenzyl ammonium chloride (each 50% active) (also available as 80% active (BTC® 2125 80 or BTC® 2125 M)); BTC® 2565 is described as alkyl dimethyl benzyl ammonium chlorides (50% active) (also available as 80% active (BTC® 2568)); BTC® 8248 (or BTC® 8358) is described as alkyl dimethyl benzyl ammonium chloride (80% active) (also available as 90% active (BTC® 8249)); ONYXIDE® 3300 is described as n-alkyl dimethyl benzyl ammonium saccharinate (95% active). (BTC® and ONYXIDE® are presently commercially available from Stepan Company, Northfield, Ill.) Polymeric quaternary ammonium salts based on these monomeric structures are also considered desirable for the present invention. One example is POLYQUAT®, described as being a 2-butenyldimethyl ammonium chloride polymer.

When present, the quaternary ammonium compound(s) may be present in any effective amount, but generally need not be present in amounts in excess of about 10% wt. based on the total weight of the composition. Preferably the germicidal quaternary ammonium compounds may be present in the inventive compositions in amounts of from about 0.001% wt. to up to about 10% wt., very preferably about 0.01-8% wt., more preferably in amounts of about 0.01-2% wt., and most preferably about 0.01-1% wt. It is particularly advantageous that the preferred germicidal cationic surfactant(s) are present in amounts of at least about 200 parts per million (ppm), preferably in amounts of from about 1 ppm to about 10,000 ppm, preferably from about 50 ppm to about 2000 ppm, more preferably in amounts of from about 100 ppm to about 1,000 ppm. Particularly preferred amounts of one or more quaternary ammonium compound(s) and preferred amounts are identified with reference to the examples.

The compositions of the invention may further include at least one further detersive surfactant, (which is preferably a nonionic surfactant) other than a germicidally effective quaternary ammonium compound. Preferably the at least one further detersive surfactant improves the microbicidal efficacy of the composition of which it forms a part, as compared to where such at least one such further detersive surfactant is absent from said composition.

In certain embodiments the treatment compositions necessarily include at least one further, detersive surfactant, although such may be considered an optional constituent according to other embodiments of the invention.

Non-limiting examples of the major surfactant types that can be used as detersive surfactants of the present invention include those which are known as anionic, nonionic, amphoteric, and zwitterionic surfactants as well as further cationic surfactants which are not primarily present to provide a microbicidal or germicidal benefit. Such include, e.g.: sulfates and sulfonates of oils and fatty acids, sulfates and sulfonates, ethoxylated alkylphenols, sulfates of alcohols, sulfates of ethoxylated alcohols, sulfates of fatty esters, sulfonates of benzene, cumene, toluene and xylene, sulfonates of condensed naphthalenes, sulfonates of dodecyl and tridecylbenzenes, sulfonates of naphthalene and alkyl naphthalene, sulfonates of petroleum, sulfosuccinamates, sulfosuccinates and derivatives, soaps, taurates, thio and mercapto derivatives, tridecyl and dodecyl benzene sulfonic acids, alkanolamides, alkanolamines, alkylaryl sulfonates, alkylaryl sulfonic acids, alkylbenzenes, amine acetates, amine oxides, amines, sulfonated amines and amides, betaine derivatives, block polymers, carboxylated alcohol or alkylphenol ethoxylates, carboxylic acids and fatty acids, ethoxylated alcohols, ethoxylated alkylphenols, ethoxylated amines and/or amides, ethoxylated fatty acids, ethoxylated fatty esters and oils, fatty esters, fluorocarbon-based surfactants, glycerol esters, glycol esters, hetocyclic-type products, imidazolines and imidazoline derivatives, isethionates, lanolin-based derivatives, lecithin and lecithin derivatives, lignin and lignin deriviatives, maleic or succinic anhydrides, methyl esters, monoglycerides and derivatives, olefin sulfonates, phosphate esters, phosphorous organic derivatives, polyethylene glycols, polymeric (polysaccharides, acrylic acid, and acrylamide) surfactants, propoxylated and ethoxylated fatty acid alcohols or alkyl phenols, protein-based surfactants, sarcosine derivatives, silicone-based surfactants, sorbitan derivatives, sucrose and glucose esters and derivatives, as well as further surfactants known to the art but not elucidated here.

Typically however the use of anionic surfactants is to be avoided as such would be expected to form insoluble complexes quaternary ammonium compound which provides a germicidal or microbicidal benefit is concurrently present.

Additional non-limiting examples of detersive surfactants that can be used to carry out the present invention include one or more nonionic surfactants, especially one or more compounds based on the condensation products of alkylene oxide groups with an organic hydrophobic compound, such as an aliphatic compound or with an alkyl aromatic compound. The nonionic synthetic organic detergents generally are the condensation products of an organic aliphatic or alkyl aromatic hydrophobic compound and hydrophilic ethylene oxide groups. Practically any hydrophobic compound having a carboxy, hydroxy, amido, or amino group with a free hydrogen attached to the nitrogen can be condensed with ethylene oxide or with the polyhydration product thereof, polyethylene glycol, to form a water soluble nonionic detergent. Further, the length of the polyethenoxy hydrophobic and hydrophilic elements may be varied to adjust these properties. Illustrative examples of such a nonionic surfactant include the condensation product of one mole of an alkyl phenol having an alkyl group containing from 6 to 12 carbon atoms with from about 5 to 25 moles of an alkylene oxide. Another example of such a nonionic surfactant is the condensation product of one mole of an aliphatic alcohol which may be a primary, secondary or tertiary alcohol having from 6 to 18 carbon atoms with from 1 to about 10 moles of alkylene oxide. Preferred alkylene oxides are ethylene oxides or propylene oxides which may be present singly, or may be both present.

Non-limiting, illustrative examples of nonionic surfactants include primary and secondary linear and branched alcohol ethoxylates, such as those based on $C_6$-$C_{18}$ alcohols which further include an average of from 2 to 80 moles of ethoxylation per mol of alcohol. Examples include the Genapol® series of linear alcohol ethoxylates from Clariant Corp., Charlotte, N.C. The 26-L series is based on the formula $RO(CH_2CH_2O)_nH$ wherein R is a mixture of linear, even carbon-number hydrocarbon chains ranging from $C_{12}H_{25}$ to $C_{16}H_{33}$ and n represents the number of repeating units and is a number of from 1 to about 12, such as 26-L-1, 26-L-1.6, 26-L-2, 26-L-3, 26-L-5, 26-L-45, 26-L-50, 26-L-60, 26-L-60N, 26-L-75, 26-L-80, 26-L-98N, and the 24-L series, derived from synthetic sources and typically contain about 55% $C_{12}$ and 45% $C_{14}$ alcohols, such as 24-L-3, 24-L-45, 24-L-50, 24-L-60, 24-L-60N, 24-L-75, 24-L-92, and 24-L-98N. From product literature, the single number following the "L" corresponds to the average degree of ethoxylation (numbers between 1 and 5) and the two digit number following the letter "L" corresponds to the cloud point in ° C. of a 1.0 wt. % solution in water.

Further examples of useful nonionic surfactants include secondary $C_{12}$-$C_{15}$ alcohol ethoxylates, including those which have from about 3 to about 10 moles of ethoxylation. Such are available in the Tergitol® series of nonionic surfactants (Dow Chemical, Midland, Mich.), particularly those in the Tergitol® "15-S-" series. Further exemplary nonionic surfactants include linear primary $C_{11}$-$C_{15}$ alcohol ethoxylates, including those which have from about 3 to about 10 moles of ethoxylation. Such are available in the Tomadol® series of nonionic surfactants under the following tradenames: Tomadol 1-3 (linear $C_{11}$ alcohol with 3 moles (average) of ethylene oxide); Tomadol 1-5 (linear $C_{11}$ alcohol with 5 moles (average) of ethylene oxide); Tomadol 1-7 (linear $C_{11}$ alcohol with 7 moles (average) of ethylene oxide); Tomadol 1-9 (linear $C_{11}$ alcohol with 9 moles (average) of ethylene oxide); Tomadol 23-1 (linear $C_{12-13}$ alcohol with 1 mole (average) of ethylene oxide); Tomadol 23-3 (linear $C_{12-13}$ alcohol with 3 moles (average) of ethylene oxide); Tomadol 23-5 (linear $C_{12-13}$ alcohol with 5 moles (average) of ethylene oxide); Tomadol 23-6.5 (linear $C_{12-13}$ alcohol with 6.6 moles (average) of ethylene oxide); Tomadol 25-12 (linear $C_{12-15}$ alcohol with 11.9 moles (average) of ethylene oxide); Tomadol 25-3 (linear ($C_{12-15}$ alcohol with 2.8 moles (average) of ethylene oxide); Tomadol 25-7 (linear $C_{12-15}$ alcohol with 7.3 moles (average) of ethylene oxide); Tomadol 25-9 (linear $C_{14-15}$ alcohol with 8.9 moles (average) of ethylene oxide); Tomadol 45-13 (linear $C_{14-15}$ alcohol with 12.9 moles (average) of ethylene oxide); Tomadol 45-2.25 (linear $C_{14-15}$ alcohol with 2.23 moles (average) of ethylene oxide); Tomadol 45-7 (linear $C_{14-15}$ alcohol with 7 moles (average) of ethylene oxide); Tomadol 91-2.5 (linear $C_{9-11}$ alcohol with 2.7 moles (average) of ethylene oxide); Tomadol 91-6 (linear $C_{9-11}$ alcohol with 6 moles (average) of ethylene oxide); Tomadol 91-8 (linear $C_{9-11}$ alcohol with 8.3 moles (average) of ethylene oxide) (Tomah Products, Inc., Milton, Wis.).

Further examples of useful nonionic surfactants include $C_6$-$C_{15}$ straight chain alcohols ethoxylated with about 1 to 13 moles of ethylene oxide, particularly those which include about 3 to about 6 moles of ethylene oxide. Examples of such nonionic surfactants include Alfonic® 810-4.5, which is described as having an average molecular weight of 356, an ethylene oxide content of about 4.85 moles and an HLB of about 12; Alfonic® 810-2, which is described as having an average molecular weight of 242, an ethylene oxide content of about 2.1 moles and an HLB of about 12; and Alfonic® 610-3.5, which is described as having an average molecular weight of 276, an ethylene oxide content of about 3.1 moles, and an HLB of 10.

A further class of nonionic surfactants which may find use in the present inventive compositions include ethoxylated octyl and nonyl phenols include those having one of the following general structural formulas:

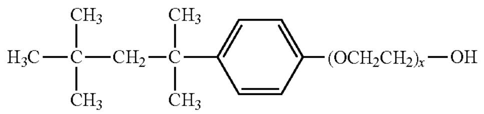

or,

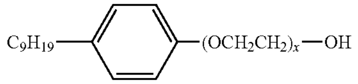

in which the $C_9H_{19}$ group in the latter formula is a mixture of branched chained isomers, and x indicates an average number of ethoxy units in the side chain. Particularly suitable non-ionic ethoxylated octyl and nonyl phenols include those having from about 7 to about 13 ethoxy groups. Such compounds are commercially available under the trade name Triton® X (Dow Chemical, Midland, Mich.), as well as under the tradename Igepal® (Rhodia, Princeton, N.J.). One such exemplary and particularly preferred surfactant is nonylphenol ethoxylate is Igepal® CO-630.

Still further examples of suitable nonionic surfactants include which may be advantageously included in the inventive compositions are alkoxy block copolymers, and in particular, compounds based on ethoxy/propoxy block copolymers. Polymeric alkylene oxide block copolymers include nonionic surfactants in which the major portion of the molecule is made up of block polymeric C2-C4 alkylene oxides. Such nonionic surfactants, while preferably built up from an alkylene oxide chain starting group, and can have as a starting nucleus almost any active hydrogen containing group including, without limitation, amides, phenols, thiols and secondary alcohols.

One group of such useful nonionic surfactants containing the characteristic alkylene oxide blocks are those which may be generally represented by the formula (A):

$$HO\text{-}(EO)_x(PO)_y(EO)_z\text{—}H \quad (A)$$

where EO represents ethylene oxide,

PO represents propylene oxide, y equals at least 15.

$(EO)_{x+z}$ equals 20 to 50% of the total weight of said compounds, and, the total molecular weight is preferably in the range of about 2000 to 15,000.

Another group of nonionic surfactants for use in the new compositions can be represented by the formula (B):

$$R\text{-}(EO,PO)_a(EO,PO)_b\text{—}H \quad (B)$$

wherein R is an alkyl, aryl or aralkyl group, where the R group contains 1 to 20 carbon atoms, the weight percent of EO is within the range of 0 to 45% in one of the blocks a, b, and within the range of 60 to 100% in the other of the blocks a, b, and the total number of moles of combined EO and PO is in the range of 6 to 125 moles, with 1 to 50 moles in the PO rich block and 5 to 100 moles in the EO rich block.

Further nonionic surfactants which in general are encompassed by formula (B) include butoxy derivatives of propylene oxide/ethylene oxide block polymers having molecular weights within the range of about 2000-5000.

Still further useful nonionic surfactants containing polymeric butoxy (BO) groups can be represented by formula (C) as follows:

$$RO\text{—}(BO)_n(EO)_x\text{—}H \quad (C)$$

wherein R is an alkyl group containing 1 to 20 carbon atoms, n is about 5-15 and x is about 5-15.

Also useful as the nonionic block copolymer surfactants, which also include polymeric butoxy groups, are those which may be represented by the following formula (D):

$$HO\text{-}(EO)_x(BO)_n(EO)_y\text{—}H \quad (D)$$

wherein n is about 5-15, preferably about 15,
x is about 5-15, preferably about 15, and
y is about 5-15, preferably about 15.

Still further useful nonionic surfactants include ethoxylated derivatives of propoxylated ethylene diamine, which may be represented by the following formula:

(E)

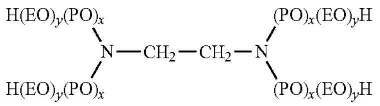

where (EO) represents ethoxy,
(PO) represents propoxy,
the amount of $(PO)_x$ is such as to provide a molecular weight prior to ethoxylation of about 300 to 7500, and the amount of (EO) is such as to provide about 20% to 90% of the total weight of said compound.

Further examples of useful nonionic surfactants are one or more amine oxides.

Exemplary amine oxides include:

A) Alkyl di (lower alkyl) amine oxides in which the alkyl group has about 10-20, and preferably 12-16 carbon atoms, and can be straight or branched chain, saturated or unsaturated. The lower alkyl groups include between 1 and 7 carbon atoms. Examples include lauryl dimethyl amine oxide, myristyl dimethyl amine oxide, and those in which the alkyl group is a mixture of different amine oxide, dimethyl cocoamine oxide, dimethyl (hydrogenated tallow) amine oxide, and myristyl/palmityl dimethyl amine oxide;

B) Alkyl di (hydroxy lower alkyl) amine oxides in which the alkyl group has about 10-20, and preferably 12-16 carbon atoms, and can be straight or branched chain, saturated or unsaturated. Examples are bis(2-hydroxyethyl) cocoamine oxide, bis(2-hydroxyethyl) tallowamine oxide; and bis(2-hydroxyethyl) stearylamine oxide;

C) Alkylamidopropyl di(lower alkyl) amine oxides in which the alkyl group has about 10-20, and preferably 12-16 carbon atoms, and can be straight or branched chain, saturated or unsaturated. Examples are cocoamidopropyl dimethyl amine oxide and tallowamidopropyl dimethyl amine oxide; and D) Alkylmorpholine oxides in which the alkyl group has about 10-20, and preferably 12-16 carbon atoms, and can be straight or branched chain, saturated or unsaturated.

Preferably the amine oxide constituent is an alkyl di (lower alkyl) amine oxide as denoted above and which may be represented by the following structure:

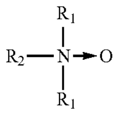

wherein each:

$R_1$ is a straight chained $C_1$-$C_4$ alkyl group, preferably both $R_1$ are methyl groups; and, $R_2$ is a straight chained $C_8$-Cis alkyl group, preferably is $C_{10\text{-}14}$ alkyl group, most preferably is a $C_{12}$ alkyl group.

Each of the alkyl groups may be linear or branched, but most preferably are linear. Technical grade mixtures of two or more amine oxides may be used, wherein amine oxides of varying chains of the $R_2$ group are present. Preferably, the amine oxides used in the present invention include $R_2$ groups which comprise at least 50% wt., preferably at least 60% wt. of $C_{12}$ alkyl groups and at least 25% wt. of $C_{14}$ alkyl groups, with not more than 15% wt. of $C_{16}$, $C_{18}$ or higher alkyl groups as the $R_2$ group.

Further specific examples of useful nonionic surfactants are alkanolamide surfactant compounds. Exemplary useful alkanolamides include one or more monoethanol amides, and diethanol amides of fatty acids having an acyl moiety which contains from about 8 to about 18 carbon atoms, and which may be represented in accordance with the formula:

$$R_1\text{—}CO\text{—}N(H)_{m-1}(R_2OH)_{3-m}$$

where $R_1$ represents a saturated or unsaturated aliphatic hydrocarbon radical of from about 7 to 21 carbon atoms, but preferably from about 11 to 17 carbon atoms; $R_2$ represents a —$CH_2$— or —$CH_2CH_2$—, and m is an integer from 1 to 3, but is preferably 1. Preferably, $R_1$ is a saturated or unsaturated aliphatic hydrocarbon radical comprising from about 11 to 17 carbon atoms, and m is 1. Specific examples of such compounds include mono-ethanol amine coconut fatty acid amide and diethanol amine dodecyl fatty acid amide. An exemplary useful and particularly preferred fatty acid amides include cocomonoethanol amide or cocodiethanolamide, which are presently commercially available under the Monamid® tradenane. Further exemplary useful alkanolamides which provide such functions include inter alia: cocamide MEA, cocamide DEA, soyamide DEA, lauramide DEA, oleamide MIPA, stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA, and mixtures thereof. Further useful alkanolamide surfactant compounds include alkanolamides, particularly fatty monoalkanolamides and fatty dialkanolamides, including one or more of those marketed under the Ninol® tradename. Further exemplary alkanolamide surfactant compounds include monoethanol amides and diethanol amides include those marketed under the trade names Alakamide® and Cyclomide® by Rhône-Poulenc Co., (Cranbury, N.J.) e.g., Cyclomide® CDD-518 described to be a nonionic surfactant based on coconut diethanolamide; Cyclomide® C212 described to be a nonionic surfactant based on coconut monoethanolamide; Cyclomide® DC212/SE described to be a nonionic surfactant based on 1:1 fatty acid diethanolamide; Cyclomide® DIN 100 described to be a nonionic surfactant based on lauric/linoleic diethanolamide; Cyclomide® DIN-295/S described to be a nonionic surfactant based on 1:1 linoleic diethanolamide; Cyclomide® DL203 described to be a nonionic surfactant based on 2:1 lauric diethanolamide.

Further specific examples of useful nonionic surfactants include alkyl polyglycosides. The alkyl polyglycosides which can be used as nonionic surfactants in the composition are generally represented by the formula:

$$R_1O(R_2O)_b(Z)_a$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6. Preferred alkyl polyglycosides have the formula 1 wherein Z is a glucose residue and b is zero. Such alkyl polyglycosides are commercially available, for example, as APG®, GLUCOPON®, or PLANTAREN® surfactants from Cogis Corp. Specific examples of such surfactants include but are not limited to: APG® 225, described to be an alkyl polyglycoside in which the alkyl group contains 8 to 10 carbon atoms and having an average degree of polymerization of 1.7; GLUCOPON® 425, described to be an alkyl polyglycoside in which the alkyl group contains 8 to 16 carbon atoms and having an average degree of polymerization of 1.48; GLUCOPON® 625, described to be an alkyl polyglycoside in which the alkyl group contains 12 to 16 carbon atoms and having an average degree of polymerization of 1.6; APG® 325, described to be an alkyl polyglycoside in which the alkyl group contains 9 to 11 carbon atoms and having an average degree of polymerization of 1.5; GLUCOPON® 600, described to be an alkyl polyglycoside in which the alkyl group contains 12 to 16 carbon atoms and having an average degree of polymerization of 1.4, PLANTAREN® 2000, described to be an alkyl polyglycoside in which the alkyl group contains 8 to 16 carbon atoms and having an average degree of polymerization of 1.4; and, PLANTAREN® 1300, described to be an alkyl polyglycoside in which the alkyl group contains 12 to 16 carbon atoms and having an average degree of polymerization of 1.6. Other examples include alkyl polyglycoside surfactant compositions which are comprised of mixtures of compounds of formula 1 wherein Z represents a moiety derived from a reducing saccharide containing 5 or 6 carbon atoms; a is a number having a value from 1 to about 6; b is zero; and R.sub.1 is an alkyl radical having from 8 to 20 carbon atoms. The compositions are characterized in that they have increased surfactant properties and an HLB in the range of about 10 to about 16 and a non-Flory distribution of glycosides, which is comprised of a mixture of an alkyl monoglycoside and a mixture of alkyl polyglycosides having varying degrees of polymerization of 2 and higher in progressively decreasing amounts, in which the amount by weight of polyglycoside having a degree of polymerization of 2, or mixtures thereof with the polyglycoside having a degree of polymerization of 3, predominate in relation to the amount of monoglycoside, said composition having an average degree of polymerization of about 1.8 to about 3. Such compositions, also known as peaked alkyl polyglycosides, can be prepared by separation of the monoglycoside from the original reaction mixture of alkyl monoglycoside and alkyl polyglycosides after removal of the alcohol. This separation may be carried out by molecular distillation and normally results in the removal of about 70-95% by weight of the alkyl monoglycosides. After removal of the alkyl monoglycosides, the relative distribution of the various components, mono-and poly-glycosides, in the resulting product changes and the concentration in the product of the polyglycosides relative to the monoglycoside increases as well as the concentration of individual polyglycosides to the total, i.e. DP2 and DP3 fractions in relation to the sum of all DP fractions. Such compositions are disclosed in U.S. Pat. No. 5,266,690, the entire contents of which are incorporated herein by reference.

Other alkyl polyglycosides which can be used in the compositions according to the invention are those in which the alkyl moiety contains from 6 to 18 carbon atoms in which and the average carbon chain length of the composition is from about 9 to about 14 comprising a mixture of two or more of at least binary components of alkylpolyglycosides, wherein each binary component is present in the mixture in relation to its average carbon chain length in an amount effective to provide the surfactant composition with the average carbon chain length of about 9 to about 14 and wherein at least one, or both binary components, comprise a Flory distribution of polyglycosides derived from an acid-catalyzed reaction of an alcohol containing 6-20 carbon atoms and a suitable saccharide from which excess alcohol has been separated.

Also useful as nonionic surfactants are ethylene oxides condensed with sorbitan fatty acid esters. Such materials are presently commercially available under the tradename TWEEN (ex. ICI) and/or CRILL (ex. Croda) which include polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate, polyoxyethylene sorbitan trioleates which are available in a variety of grades, and with differing amounts of polyoxylethylene groups per molecule.

Further useful nonionic surfactants include silicone-containing surfactants. A preferred class of silicone containing surfactants are the polyalkylene oxide polysiloxanes having a dimethyl polysiloxane hydrophobic moiety and one or more hydrophilic polyalkylene side chains.

Preferred silicone-containing surfactants include those according to the general formula (1):

$$R^1—(CH_3)_2SiO—[(CH_3)_2SiO]_a—[(CH_3)R^1)SiO]_b—Si(CH_3)_2—R^1 \quad (1)$$

wherein (a+b) is about 1 to about 50, specifically about 3 to about 30, more specifically about 10 to about 25, and each $R^1$ is the same or different and is selected from the group consisting of methyl and a poly(ethyleneoxide/propyleneoxide) copolymer group having the general formula (2):

$$—(CH_2)_nO(C_2H_4O)_c(C_3H_6O)_dR^2 \quad (2)$$

with at least one $R^1$ being a poly(ethyleneoxide/propyleneoxide) copolymer group, and wherein n is 3 or 4; total c (for all polyalkyleneoxy side groups) has a value of 1 to about 100, preferably from about 6 to about 100; total d is from 0 to about 14, preferably from 0 to about 3; and more preferably d is 0; total c+d has a value of from about 5 to about 150, preferably from about 9 to about 100 and each $R^2$ is the same or different and is selected from the group consisting of hydrogen, an alkyl having 1 to 4 carbon atoms, and an acetyl group, specifically hydrogen and methyl group. In one embodiment, each polyalkylene oxide polysiloxane has at least one $R^1$ group being a poly(ethyleneoxide/propyleneoxide) copolymer group. Examples of this type of surfactant are the SILWET Hydrostable 68, 611, and 212 (ex. Momentive Performance Materials.)

Non-limiting examples of further detersive surfactants which may be included in the treatment compositions of the invention include zwitterionic and amphoteric surfactants. Zwitterionic surfactants may also be present either by themselves or in admixture with another ionic surfactant providing there are no troublesome interactions. Typical examples of amphoteric or zwitterionic surfactants are alkyl betaines, alkyl amidobetaines, aminopropionates, aminoglycinates, imidazolinium betaines and sulfobetaines. Within this group, alkyl betaines and alkyl amidobetaines are particularly preferred. Alkyl betaines are known surfactants which are mainly produced by carboxyalkylation, preferably carboxymethylation of aminic compounds. Typical examples are the carboxymethylation products of hexyl methyl amine, hexyl dimethyl amine, octyl dimethyl amine, decyl dimethyl amine, dodecyl methyl amine, dodecyl dimethyl amine, dodecyl ethyl methyl amine, C12/14 cocoalkyl dimethyl amine, myristyl dimethyl amine, cetyl dimethyl amine, stearyl dimethyl amine, stearyl ethyl methyl amine, oleyl dimethyl amine, C16/18 tallow alkyl dimethyl amine and technical mixtures thereof Alkyl amidobetaines which represent carboxyalkylation products of amidoamines are also suitable. Typical examples are reaction products of fatty acids containing 6 to 22 carbon atoms, namely caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof, with N,N-dimethylaminoethyl amine, N,N-dimethylaminoproply amine, N,N-diethylaminoethyl amine and N,N-diethylaminoproply amine which are condensed with sodium chloroacetate. The condensation product of C8/18 cocofatty acid-N,N-dimethylaminopropyl amide with sodium chloroacetate is preferably used.

Further specific examples of particular amphoteric surfactants which may be used in the treatment compositions of the invention include one or more amphoteric surfactants. Exemplary amphoteric surfactants include alkylampho (mono)acetales, alkylampho(di)acetates, alkylampho(mono) propionates, and alkylampho(di)propionates. Examples of these amphoteric surfactants can be found under the tradename Miranol from Rhodia (Cranbury, N.J.). Some examples include Miranol C2M-Conc. NP, described to be disodium cocoamphodiacetate; Miranol FA-NP, described to be sodium cocoamphotacetate; Miranol DM, described to be sodium steroamphoacetate; Miranol HMA, described to be sodium lauroamphoacetate; Miranol C2M, described to be cocoamphodiprioponic acid; Miranol C2M-SF, described to be disodium cocoamphodiproprionate; Miranol CM-SF Conc., described as being cocoamphopropriate: Mirataine H2C-HA, described as sodium lauiminodiproprionate; Miranol Ultra L-32, described as sodium lauroamphoacetate; and Miranol Ultra C-37, described as sodium cocoamphoacetate. Other amphoteric surfactants are also available under the tradename Amphoterge from Lonza (Fair Lawn, N.J.) such as Amphoterge K described to sodium cocoamphoproprionate; Amphoterge K-2, described as disodium cocoamphodiproprionate; Amphoterge W, described to be sodium cocoamphoacetate; and Amphoterge W-2, described to be disodium cocoamphodiacetate.

Further useful amphoteric surfactants include those which may be represented by the following general formula

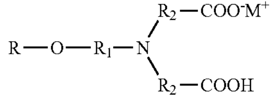

in which, R represents a $C_4$ to $C_{24}$ alkyl group, and is preferably a C10 to C16 alkyl group, R1 and R2 independently represent a $C_1$ to $C_8$ alkyl group, is preferably $—CH_2CH_2—$ or $—CH_2CH_2CH_2—$, and M may be any salt-forming anion which permits water solubility or water miscibility of the compound, e.g., chloride, bromide, methosulfate, ethosulfate, lactate, saccharinate, acetate or phosphate. Such compounds are presently commercially available, such as those marketed in the Tomamine Amphoteric series of amphoteric surfactants, ex. Air Products Inc.

While the one or more detersive surfactants may be present in any effective amount which may be observed to improve the microbicidal efficacy of the system of the essential constituents, these one or more surfactants, when present, are advantageously present in an amount of from about 0.001-15% wt., preferably from about 0.01-10% wt. and particularly preferably from about 0.05-5% wt., based on the total weight of the treatment composition within which they are present. When a quaternary ammonium compound(s) is/are present, the foregoing amounts, the quaternary ammonium compound(s) should not be considered in the weight percentages of the one or more further optional detersive surfactants, although such quaternary ammonium compound(s) are often classified as cationic surfactants. Furthermore, the selection of any one or more further optional detersive surfactants should be made to ensure that it/they do not deleteriously diminish the microbicidal properties of the compositions of the invention.

The inventive compositions most desirably, although not always essentially, include at least one nonionic surfactant. An example of an especially preferred nonionic surfactant is at least one alcohol alkoxylate (e.g, ethoxylate, propoxylate) based nonionic surfactant in an amount of from about 0.01-10% wt. In order of increasing preference, when present, the at least one nonionic surfactant comprises in % wt. at least about 0.025, 0.05, 0.075, 0.1, 0.15, 0.2, 0.25, 0.3, 0.4, 0.5, 0.6, 0.75, 0.8, 0.9, 1, 1.1, 1.2, 1.3, 1.4 and 1.5% wt. and similarly in order of increasing preference the at least one nonionic surfactant comprises, in % wt., not more than about 10, 9, 8, 7.5, 7, 6, 5, 4.75, 4.5, 4, 3.75, 3.5, 3.25, 3, 2.75 and 2% wt. based on the total weight of composition of which they form a part. In certain embodiments at least one nonionic surfactant is necessarily present.

In certain embodiments, the sole surfactants present in the compositions are one or more of the cationic surfactants described above, and/or one or more of the nonionic surfactants described above.

In certain embodiments the sole surfactant(s) present is one or more cationic surfactants.

In certain embodiments the sole additional surfactant(s) present is one or more nonionic surfactants.

In certain embodiments, the sole surfactants present in the compositions are one or more of the cationic surfactants described above, and/or one or more of the nonionic surfactants described above.

The pH of the treatment compositions is preferably established and thereafter maintained at a desired pH or within a bounded pH range. Thus, a reasonable degree of flexibility in formulating compositions of the invention is provided by judicious control of the pH and the amount of the lower alkyl monohydric alcohol present. Specific reference is made to the example formulations described hereinafter which demonstrate this effect. The pH of the inventive compositions is at least 5, but is preferably greater and in certain particularly preferred embodiments is substantially alkaline. While the pH of the composition may be 5 or greater, preferably the pH of the compositions is at least about 6, and more preferably is in the range of from about 7-14, especially in the range of about 9-12. Thus in preferred embodiments the pH of the treatment compositions (and/or microbicidal control system) is at least about 6, and in order of increasing preference is at least 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9.9, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5. In preferred embodiments, and in order of increasing preference the pH of the treatment compositions (and/or microbicidal control system) is not in excess of: 12.5, 12.4, 12.3, 12.2, 12.1, 12, 11.9, 11.8, 11.7, 11.6, 11.5, 11.4, 11.3, 11.2, 11.1, 11, 10.9, 10.8, 10.7, 10.6, 10.5, 10.4, 10.3, 10.2, 10.1, 10, 9.9, 9.8, 9.7, 9.6, 9.5. It is expected that compositions of the invention may have lower pHs, in the range of 1-14 if desired; however preferred pHs are indicated in the foregoing ranges and are demonstrated by the Examples. In certain preferred embodiments the pH of the compositions is less than 11. The pH of the surface treatment compositions may be established, adjusted and/or maintained by the addition of an effective amount of a pH adjustment constituent.

Optionally but preferably the treatment compositions of the invention include a pH adjusting constituent which may be used to establish and/or maintain, viz., buffer, a treatment composition at a desired pH or within a bounded pH range. Essentially any material which may increase or decrease the pH of the treatment composition is suitable as a pH adjusting constituent. Suitable pH adjusting constituents are one or more acids and/or bases whether such be based on organic and/or inorganic compounds or materials. By way of non-limiting example, pH adjusting agents include phosphorus containing compounds, monovalent and polyvalent salts such as of silicates, carbonates, and borates, certain acids and bases, tartrates and certain acetates. Further exemplary pH adjusting agents include mineral acids, basic compositions, and organic acids, which are typically required in only minor amounts. By way of further non-limiting example, pH buffering compositions include the alkali metal phosphates, polyphosphates, pyrophosphates, triphosphates, tetraphosphates, silicates, metasilicates, polysilicates, carbonates, hydroxides, and mixtures of the same. Certain salts, such as the alkaline earth phosphates, carbonates, and hydroxides, can also function as buffers. It may also be suitable to use as buffers such materials as aluminosilicates (zeolites), borates, aluminates and certain organic materials such as gluconates, succinates, maleates, citrates, and their alkali metal salts. Particularly useful and preferred is citric acid and metal salts thereof such as sodium citrate which are widely available and which are effective in providing these pH adjustment and buffering effects. Further exemplary and useful pH adjusting constituents include monoalkanolamines, dialkanolamines, trialkanolamines, and alkylalkanolamines such as alkyl-dialkanolamines, and dialkyl-monoalkanolamines. Such may also function as detersive surfactants. The alkanol and alkyl groups are generally short to medium chain length, that is, from 1 to 7 carbons in length. For di-and trialkanolamines and dialkyl-monoalkanolamines, these groups can be combined on the same amine to produce for example, methylethylhydroxypropylhydroxylamine. One of ordinary skill in the art can readily ascertain other members of this group. Preferred alkanolamines include monoethanolamine, triethanolamine and mixtures thereof. Preferred respective ratios of monoethanolamine to triethanolamine are disclosed in the examples.

The use of a citrate as a pH adjusting agent, e.g, sodium citrate, or citric acid, is preferred, as, while not wishing to be bound by the following, it is hypothesized that the presence of a citrate in the compositions of the invention facilitate the availability of zinc ions in the compositions. It is hypothesized that the disassociation of the zinc ions from the zinc ion source material which releases zinc ions into the treatment composition into the treatment composition may be reversible reaction, and the concurrent presence of citrates in the compositions provides for the formation of zinc salts of citrates (or of citric acid) which is also believed to be a reversible reaction, but as the zinc of the zinc salts of the citrates may be more easily disassociated than the disassociation of zinc from the zinc ion source material, such may increase the concentration of available free zinc ions in the composition. Thus, it is preferred that the pH adjusting agent comprise a citrate material (or citric acid), and preferably further, that such be present in at least a molar equivalent or excess of the zinc ion source material. Of course, where the zinc ion source material includes, or preferably consists of zinc salt of a citrate, such may satisfy this hypothesis.

When present, the one or more pH adjusting constituents are included in amounts which are effective in establishing and/or maintaining the pH of a treatment composition at the desired pH value or within a range of pH values. Advantageously the one or more pH adjusting constituents comprise from about 0.001-2.5% wt., preferably from about 0.01-1.5% wt. of the treatment composition of which the one or more pH adjusting constituents form a part. Preferred pH adjusting constituents include those demonstrated in or more of the Examples. In certain preferred embodiments, one or more pH adjusting constituents are necessarily present and are to be understood as essential constituents of the treatment compositions.

The compositions of the invention may include one or more further optional constituents or materials which impart a desired technical and/or aesthetic features of the inventive compositions.

Although the compositions of the invention are largely aqueous in certain embodiments one or more organic solvents may be present. Such are differentiated from the essential alkyl aliphatic monohydric alcohol constituent. Such further optional organic solvents may include one or more of: alcohols other than the essential lower alkyl aliphatic monohydric alcohol described previously, glycols, acetates, ether acetates, glycerols, as well as polyethylene glycols and glycol ethers. Mixtures of these further optional organic solvents can also be used. Typically such further one or more organic solvents are ones which have no appreciable microbicidal effect and are thus differentiated from the essential alkyl aliphatic monohydric alcohol constituent. Non-limiting examples of useful glycol ethers and examples include those glycol ethers having the general structure $R_a—O—[CH_2—CH(R)—(CH_2)—O]_n—H$, wherein $R_a$ is $C_{1-20}$ alkyl or alkenyl, or a cyclic alkane group of at least 6 carbon atoms, which may be fully or partially unsaturated or aromatic; n is an integer from 1 to 10, preferably from 1 to 5; each R is selected from H or $CH_3$; and a is the integer 0 or 1. Specific and preferred solvents are selected from propylene glycol methyl ether, dipropylene glycol methyl ether, tripropylene glycol methyl ether, propylene glycol n-propyl ether, ethylene glycol n-butyl ether, diethylene glycol n-butyl ether, diethylene glycol methyl ether, propylene glycol, ethylene glycol, diethylene glycol monoethyl ether acetate and the like. When present such further optional one or more organic solvents may be present in any effective amount, preferably in amounts of between about 0.001-10% wt., and preferably between about 0.01-5% wt. based on the total weight of the treatment composition of which they form a part.

The treatment compositions of the invention may optionally include one or more acids, which include not only organic and inorganic acids but also acid salts of organic acids. Preferred examples of the organic acid to be used in the present invention include linear aliphatic acids such as formic acid, acetic acid, propionic acid, butyric acid and valeric acid; dicarboxylic acids such as oxalic acid, malonic acid, succinic acid, glutaric acid, adipic acid, pimelic acid, fumaric acid and maleic acid; acidic amino acids such as glutamic acid and aspartic acid; and hydroxy acids such as glycolic acid, lactic acid, hydroxyacrylic acid, alpha-hydroxybutyric acid, glyceric acid, tartronic acid, malic acid, tartaric acid and citric acid, as well as acid salts of these organic acids. Exemplary inorganic acids include phosphoric acid, potassium dihydrogenphosphate, sodium dihydrogenphosphate, sodium sulfite, potassium sulfite, sodium pyrosulfite (sodium metabisulfite), potassium pyrosulfite (potassium metabisulfite), acid sodium hexametaphosphate, acid potassium hexametaphosphate, acid sodium pyrophosphate, acid potassium pyrophosphate and sulfamic acid. These acids can be used singly or as a mixture of two or more inorganic and/or organic acids. Such one or more acids may be used to adjust the pH of the inventive compositions, and/or buffer the pH of the treatment compositions. When present, these may be included in effective amounts. Particularly useful is citric acid and metal salts thereof such as sodium citrate which are widely available and which are effective in providing these pH adjustment and buffering effects. These should be screened however to ensure that they do not undesirably complex with or in other ways deactivate any quaternary ammonium compound(s) which may be present.

The treatment compositions of the invention may also include one or more further compounds, constituents or materials which provide an ancillary microbicidal benefit or effect. These are distinguished from the essential constituents of the invention described above. When present, they may be included in amounts which are effective in order to provide an ancillary microbicidal benefit. Non-limiting examples of such materials include non-cationic microbicidal agents which are particularly useful in the present invention: pyrithiones (especially zinc pyrithione which is also known as ZPT), dimethyldimethylol hydantoin (Glydant), methylchloroisothiazolinone/methylisothiazolinone (Kathon CG), sodium sulfite, sodium bisulfite, imidazolidinyl urea (Germall 115), diazolidinyl urea (Germaill II), benzyl alcohol, 2-bromo-2-nitropropane-1,3-diol (Bronopol), formalin (formaldehyde), iodopropenyl butylcarbamate (Polyphase P100), chloroacetamide, methanamine, methyldibromonitrile glutaronitrile (1,2-Dibromo-2,4-dicyanobutane or Tektamer), glutaraldehyde, 5-bromo-5-nitro-1,3-dioxane (Bronidox), phenethyl alcohol, o-phenylphenol/sodium o-phenylphenol, sodium hydroxymethylglycinate (Suttocide A), polymethoxy bicyclic oxazolhdine (Nuosept C), dimethoxane, thimersal dichlorobenzyl alcohol, captan, chlorphenenesin, dichlorophene, chlorbutanol, glyceryl laurate, halogenated diphenyl ethers like 2,4,4-trichloro-2-hydroxy-diphenyl ether (Triclosan or TCS), 2,2-dihydroxy-5,5-dibromo-diphenyl ether, phenolic compounds like phenol, 2-methyl phenol, 3-methyl phenol, 4-methyl phenol, 4-ethyl phenol, 2,4-dimethyl phenol, 2,5-dimethyl phenol, 3,4-dimethyl phenol, 2,6-dimethyl phenol, 4-n-propyl phenol, 4-n-butyl phenol, 4-n-amyl phenol, 4-tert-amyl phenol, 4-n-hexyl phenol, 4-n-heptyl phenol, mono-and poly-alkyl and aromatic halophenols such as p-chlorophenol, methyl p-chlorophenol, ethyl p-chlorophenol, n-propyl p-chlorophenol, n-butyl p-chlorophenol, n-amyl p-chlorophenol, sec-amyl p-chlorophenol, n-hexyl p-chlorophenol, cyclohexyl p-chlorophenol, n-heptyl p-chlorophenol, n-octyl p-chlorophenol, o-chlorophenol, methyl o-chlorophenol, ethyl o-chlorophenol, n-propyl o-chlorophenol, n-butyl o-chlorophenol, n-amyl o-chlorophenol, tert-amyl o-chlorophenol, n-hexyl o-chlorophenol, n-heptyl o-chlorophenol, o-benzyl p-chlorophenol, o-benzyl-m-methyl p-chlorophenol, o-benzyl-m, m-dimethyl p-chlorophenol, o-phenylethyl p-chlorophenol, o-phenylethyl-m-methyl p-chlorophenol, 3-methyl p-chlorophenol, 3,5-dimethyl p-chlorophenol, 6-ethyl-3-methyl p-chlorophenol, 6-n-propyl-3-methyl p-chlorophenol, 6-iso-propyl-3-methyl p-chlorophenol, 2-ethyl-3,5-dimethyl p-chlorophenol, 6-sec-butyl-3-methyl p-chlorophenol, 2-iso-propyl-3,5-dimethyl p-chlorophenol, 6-diethylmethyl-3-methyl p-chlorophenol, 6-iso-propyl-2-ethyl-3-methyl p-chlorophenol, 2-sec-amyl-3,5-dimethyl p-chlorophenol 2-diethylmethyl-3,5-dimethyl p-chlorophenol, 6-sec-octyl-3-methyl p-chlorophenol, p-chloro-m-cresol, p-bromophenol, methyl p-bromophenol, ethyl p-bromophenol, n-propyl p-bromophenol, n-butyl p-bromophenol, n-amyl p-bromophenol, sec-amyl p-bromophenol, n-hexyl p-bromophenol, cyclohexyl p-bromophenol, o-bromophenol, tert-amyl o-bromophenol, n-hexyl o-bromophenol, n-propyl-m, m-dimethyl o-bromophenol, 2-phenyl phenol, 4-chloro-2-methyl phenol, 4-chloro-3-methyl phenol, 4-chloro-3,5-dimethyl phenol, 2,4-dichloro-3,5-dimethylphenol, 3,4,5,6-terabromo-2-methylphenol, 5-methyl-2-pentylphenol, 4-isopropyl-3-methylphenol, para-chloro-meta-xylenol, dichloro meta xylenol, chlorothymol, 5-chloro-2-hydroxydiphenylmethane, resorcinol and its derivatives including methyl resorcinol, ethyl resorcinol, n-propyl resorcinol, n-butyl resorcinol, n-amyl resorcinol, n-hexyl resorcinol, n-heptyl resorcinol, n-octyl resorcinol, n-nonyl resorcinol, phenyl resorcinol, benzyl resorcinol, phenylethyl resorcinol, phenylpropyl resorcinol, p-chlorobenzyl resorcinol, 5-chloro 2,4-dihydroxydiphenyl methane, 4-chloro 2,4-dihydroxydiphenyl methane, 5-bromo 2.4-dihydroxydiphenyl methane, and 4-bromo 2,4-dihydroxydiphenyl methane, bisphenolic compounds like 2,2-methylene his (4-chlorophenol), 2,2-methylene bis (3,4,6-trichlorophenol). 2,2-methylene his (4-chloro-6-bromophenol), his (2-hydroxy-3,5-dichlorophenyl) sulphide, and his (2-hydroxy-5-chlorobenzyl)sulphide, benzoic esters (parabens) like methylparaben, propylparaben, butylparaben, ethylparaben, isopropylparaben, isobutylparaben, benzylparaben, sodium methylparaben, and sodium propylparaben, halogenated carbanilides (e.g., 3,4, 4-trichlorocarbanilides (Triclocarban or TCC), 3-trifluoromethyl-4,4-dichlorocarbanilide, 3,3,4-trichlorocarbanilide, etc.).

Of these, preferred are phenol based non-cationic microbicidals, especially those based on one or more phenolic compounds, particularly 2-hydroxydiphenyl compounds which may be exemplified by the following classes of compounds:

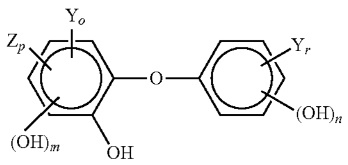

wherein Y is chlorine or bromine. Z is $SO_2$ H, $NO_2$, or $C_1$-$C_4$ alkyl, r is 0 to 3, o is 0 to 3, p is 0 or 1, m is 0 or 1, and n is 0 or 1. In preferred embodiments. Y is chlorine or bromine, m is 0, n is 0 or 1, o is 1 or 2, r is 1 or 2, and p is 0, and according to especially preferred embodiments, Y is chlorine, in is 0, n is 0, o is 1, r is 2, and p is 0.

Particularly useful 2-hydroxydiphenyl compounds include those which may be represented by the structure:

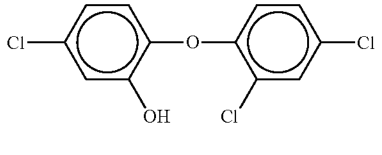

which is commonly referred to as "TRICLOSAN" and which is presently commercially available from Ciba Specialty Chemicals Corp., as well as halogenated carbanilides, e.g., TCC.

Further exemplary useful phenolic based disinfecting agents include 2,2'-hydroxy-5,5'-dibromo-diphenyl ether which may be represented by the structure:

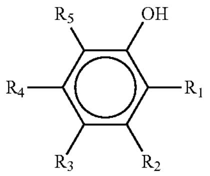

wherein $R_1$ is hydro, hydroxy, $C_1$-$C_4$ alkyl, chloro, nitro, phenyl, or benzyl; $R_2$ is hydro, hydroxy. $C_1$-$C_6$ alkyl, or halo; $R_3$ is hydro, $C_1$-$C_6$ alkyl, hydroxy, chloro, nitro, or a sulfur in the form of an alkali metal salt or ammonium salt; $R_4$ is hydro or methyl, and R is hydro or nitro. Halo is bromo or, preferably, chloro.

Specific examples of phenol derivatives include, but are not limited to, chlorophenols (o-, m-, p-), 2,4-dichlorophenol, p-nitrophenol, picric acid, xylenol, p-chloro-m-xylenol, cresols (o-, m-, p-), p-chloro-m-cresol, pyrocatechol, resorcinol, 4-n-hexylresorcinol, pyrogallol, phloroglucin, carvacrol, thymol, p-chlorothymol, o-phenylphenol, o-benzylphenol, p-chloro-o-benzylphenol, phenol, 4-ethylphenol, and 4-phenolsulfonic acid.

Still further useful phenol derivatives include those which may be represented by the structure:

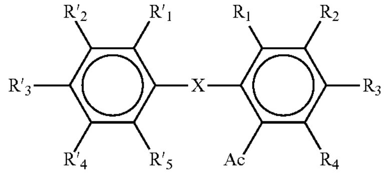

wherein X is sulfur or a methylene group, $R_1$ and $R'_1$ are hydroxy, and $R_2$, $R'_2$, $R_3$, $R'_3$, $R_4$, $R'_4$, $R_5$, and $R'_5$, independent of one another, are hydro or halo. Specific, nonlimiting examples of diphenyl compounds are hexachlorophene, tetrachlorophene, dichlorophene, 2,3-dihydroxy-5,5'-dichlorodiphenyl sulfide, 2,2'-dihydroxy-3,3',5,5'-tetrachlorodiphenyl sulfide, 2,2'-dihydroxy-3,5',5,5',6,6'-hexachlorodiphenyl sulfide, and 3,3'-dibromo-5,5'-dichloro-2,2'-dihydroxydiphenylamine. Of the foregoing, a particularly useful phenol derivative is commonly referred to as triclocarban, or 3,4,4'-trichlorocarbanilide as well as derivatives thereto. When present, one or more such further compounds, constituents or materials which provide an ancillary microbicidal benefit or effect may be present in effective amounts, e.g., in amounts of up to about 5% wt., although depending upon the efficacy of one or more selected such further compounds, constituents or materials are usually effective in reduced amounts, e.g., 0.001-2% wt. of the treatment composition.

The treatment compositions of the invention may optionally include a fragrance constituent, which may be based on natural and/or synthetic fragrances and most commonly are mixtures or blends of a plurality of such fragrances, optionally in conjunction with a carrier such as an organic solvent or a mixture of organic solvents in which the fragrances are dissolved, suspended or dispersed. Such may be natural fragrances, e.g, natural extracts of plants, fruits, roots, stems, leaves, wood extracts, e.g. terpineols, resins, balsams, animal raw materials, e.g., civet and beaver, as well as typical synthetic perfume compounds which are frequently products of the ester, ether, aldehyde, ketone, alcohol and hydrocarbon type, e.g., benzyl acetate, linalyl acetate, citral, citronellal, methyl cedryl ketone, eugenol, isoeugenol, geraniol, linalool, and typically it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, labolanum oil and lavendin oil. When present in a treatment composition, in accordance with certain of the preferred embodiments, the fragrance constituent may be present in any effective amount such that it can be discerned by a consumer of the composition, however such is advantageously present in amounts of up to about 1% wt., preferably are present in amounts of from about 0.00001% wt. to about 0.5% wt., and most preferably is present in an amount of from about 0.0001% wt. to 0.5% wt. based on the total weight of the treatment composition of which it forms a part.

A further optional constituent of the treatment compositions of the invention include colorant, such as dyes and pigments which may be used to impart a color to the compositions of which they form a part.

The treatment compositions of the invention may also optionally include a preservative constituent which is used to control undesired microorganisms within the treatment composition particularly when the treatment composition is in long-term storage and at elevated temperatures. While these are normally not present due to the microbicidal efficacy of the compositions themselves as taught herein, such ancillary preservative constituents may be included in minor but effective amounts. Nonlimiting examples include one or more of parabens, including methyl parabens and ethyl parabens, glutaraldehyde, formaldehyde, 2-bromo-2-nitropropoane-1,3-diol, 5-chloro-2-methyl-4-isothiazolin-3-one, 2-methyl-4-isothiazoline-3-one, and mixtures thereof. One exemplary composition is a combination 5-chloro-2-methyl-4-isothiazolin-3-one and 2-methyl-4-isothiazolin-3-one where the amount of either component may be present in the mixture anywhere from 0.001 to 99.99 weight percent, based on the total amount of the preservative. Further exemplary useful preservatives include those which are commercially including a mixture of 5-chloro-2-methyl-4-isothiazolin-3-one and 2-methyl-4-isothiazolin-3-one marketed under the trademark KATHON® CG/ICP as a preservative composition presently commercially available from Rohm and Haas (Philadelphia, Pa.).

A further optional constituent in the inventive treatment compositions is one or more chelating agents. Exemplary useful chelating agents include those known to the art, including by way of non-limiting example; aminopolycarboxylic acids and salts thereof wherein the amino nitrogen has attached thereto two or more substituent groups. Preferred chelating agents include acids and salts, especially the sodium and potassium salts of ethylenediaminetetraacetic acid, diethylenetriaminepentaacetic acid, N-hydroxyethylethylenediaminetriacetic acid, and of which the sodium salts of ethylenediaminetetraacetic acid may be particularly advantageously used. Such chelating agents may be omitted, or they may be included in generally minor amounts such as from about 0.001-0.5% wt. based on the weight of the chelating agents and/or salt forms thereof. When present, advantageously, such chelating agents are included in the present inventive composition in amounts from about 0.001-5% wt., but are most desirably present in reduced weight percentages from about 0.01-0.5% wt.

The amounts or presence of chelating agents should be carefully controlled and may in some preferred embodiments are excluded from the treatment compositions. This is due the fact that the presence of chelating agents may undesirably form insoluble complexes with the zinc ions present in the compositions, and thus reduce or remove their availability in the treatment compositions.

When one or more such further optional constituents are present in the treatment compositions, preferably their cumulative amount does not exceed about 25% wt. and preferably does not exceed about 20% wt., of the treatment composition of which they form a part.

The inventive compositions are preferably liquids which have a viscosity in the range of about 100 centipoise ("cP") or less, preferably and in order of increasing preference, viscosities of about 75 cP, 50 cP, 25 cP, 20 cP, 15 cP, 10 cP, 5 cP, 3 cP, 2 cP, and 1 cP, when measured using conventional quantitative method, e.g., as measured at 20° C. or 25° C. by a Brookfield Type LVT or Type RVT viscometer using a standard spindle provided by that manufacturer and measuring the samples at room temperature (20-25° C.).

As the treatment compositions taught herein are used to treat inanimate surfaces including porous and nonporous surfaces and are not provided as a topical skin treatment composition or personal care composition or for that matter as a wound dressing or a preparation for use in wound dressings, the treatment compositions most preferably exclude (unless already described previously) as constituents known-art certain additives and adjuvants which are conventional in the cosmetic, pharmaceutical or dermatological field, specifically hydrophilic or lipophilic gelling agents, hydrophilic or lipophilic active agents, humectants, opacifiers, light stabilizers including UV absorbers, and Polyquaternium type polymers.

The treatment compositions most preferably exclude (unless already described previously) thickener components especially one or more of polysaccharide thickeners such as cellulose, alkyl celluloses, alkoxy celluloses, hydroxy alkyl celluloses, naturally occurring polysaccharide polymers such as xanthan gum, guar gum, locust bean gum, tragacanth gum, or derivatives thereof, polycarboxylate polymers, polyacrylamides, clays, and mixtures thereof.

The treatment compositions of the invention are not provided with an aerosol propellant gas or constituent, and are not packaged or sold as vendible articles in pressured containers, e.g., aerosol canisters. The surface treatment compositions are pourable and pumpable, and may be dispensed by pumping the composition through a manually operated or a power driven (e.g., motor driven, pressure driven) dispensing device, such as a sprayer, viz "trigger" sprayer or spray pump affixed to a container containing a quantity of the surface treatment composition. The surface treatment composition may also be a pourable composition which may be dispensed from the open end of a suitable flask, bottle or other container, or may be dispensed via a suitable nozzle or spout, e.g., which may be operated by either inversion of the container, and optionally compressing some or part of the container, so to expel it from the container to a surface to be treated. Between such dispensing operations; however, the contents of such a container which includes the surface treatment composition are not pressurized. Thus a further aspect of the invention provides a closed container containing the inventive composition as described herein.

Thus a further aspect of the invention provides a closed container containing the inventive composition as described herein.

The treatment compositions of the invention may also be supplied within a water dispersible, water miscible or water soluble sachet or pouch or water-soluble package; such may be formed from a water soluble material, such as a water soluble or water dispersible polymeric film (e.g. polyvinyl alcohol), or alternately may be formed from a water insoluble material, such as a water insoluble polymeric film. Additionally the sachet, pouch or package may be formed in a manner where only part of the sachet is physically breachable or only part of the sachet, pouch or package is water soluble or dispersible. Thus a further aspect of the invention provides a closed, a water dispersible, a water miscible or a water soluble sachet or pouch containing the inventive composition as described herein.

The treatment compositions can also be applied to a hard surface by using a wet wipe. The wipe can be of a woven or non-woven nature. Fabric substrates can include nonwoven or woven pouches, sponges, in the form of abrasive or non-abrasive cleaning pads. Such fabrics are known commercially in this field and are often referred to as wipes. Such substrates can be resin bonded, hydroentanged, thermally bonded, meltblown, needlepunched or any combination of the former.

The nonwoven fabrics may be a combination of wood pulp fibers and textile length synthetic fibers formed by well known dry-form or wet-lay processes. Synthetic fibers such as rayon, nylon, orlon and polyester as well as blends thereof can be employed. The wood pulp fibers should comprise about 30 to about 60 percent by weight of the nonwoven fabric, preferably about 55 to about 60 percent by weight, the remainder being synthetic fibers. The wood pulp fibers provide for absorbency, abrasion and soil retention whereas the synthetic fibers provide for substrate strength and resiliency.

The substrate of the wipe may also be a film forming material such as a water soluble polymer. Such self-supporting film substrates may be sandwiched between layers of fabric substrates and heat sealed to form a useful substrate. The free standing films can be extruded utilizing standard equipment to devolatilize the blend. Casting technology can be used to form and dry films, or a liquid blend can be saturated into a carrier and then dried in a variety of known methods.

The treatment compositions of the present invention are absorbed onto the wipe to form a saturated wipe and sold as a vendible product. The wipe can then be sealed individually in a pouch which can then be opened when needed or a multitude of wipes can be placed in a container for use on an as-needed basis. The container, when closed, is sufficiently sealed to prevent evaporation of any components from the compositions. Thus a further aspect of the invention provides a closed container containing one or more wipes which include the treatment composition as described herein.

The treatment compositions of the present invention can also be applied to foams and sponges, such as open celled or closed celled sponges which may be based on naturally occurring or synthetically produced polymers, e.g., hydrophobic polymer sponges such as based on one or more polyolefins, e.g., polyurethane, as well as hydrophilic polymer foams, e.g. those based on regenerated cellulose, or melamine-formaldehyde resins, as well as natural sponges. The specific type of sponge should be selected to be compatible with the type of treatment composition with which it will be used.

The treatment compositions of the invention may be used to provide or impart a microbicidal effect on treated inanimate surfaces. Preferably the surface treatment compositions are characterized in exhibiting a microbicidal benefit when tested against one or more challenge microorganisms according to one or more of the following standardized test protocols: ASTM E1052-96(2002) Standard Test Method for Efficacy of Antimicrobial Agents against Viruses in Suspension, or ASTM E1053-11 Standard Test Method to Assess Virucidal Activity of Chemicals Intended for Disinfection of Inanimate, Nonporous Environmental Surfaces, or European Standard Surface Test, EN13697 or AOAC Germicidal Spray Products as Disinfectant Test Method, AOAC Index, $17^{th}$ Ed. (2000). In particularly preferred embodiments the treatment compositions exhibit a high degree of microbicidal efficacy against various undesirable microorganisms (sometimes referred to as 'pathogens') including various bacteria, viruses, and fungi. In particularly preferred embodiments treatment compositions of the invention exhibit a high degree of microbicidal efficacy against poliovirus type 1 (Sabin) ("PV1").

The surface treatment compositions may be applied to inanimate surfaces in order to impart a cleaning effect thereto, but preferably are applied to impart a microbicidal benefit thereto. Inanimate surfaces include hard surfaces, which are typically nonporous hard surfaces. By way of example, hard surfaces include surfaces composed of refractory materials such as: glazed and unglazed tile, brick, porcelain, ceramics as well as stone including marble, granite, and other stones surfaces; glass; metals; plastics e.g. polyester, vinyl; fiberglass, Formica®, Corian® and other hard surfaces known to the industry. Hard surfaces which are to be particularly denoted are lavatory fixtures, lavatory appliances (toilets, bidets, shower stalls, bathtubs and bathing appliances), wall and flooring surfaces especially those which include refractory materials and the like. Further hard surfaces which are particularly denoted are those associated with kitchen environments and other environments associated with food preparation. Hard surfaces include those associated with hospital environments, medical laboratories and medical treatment environments. Inanimate surfaces which may be treated by the surface treatment compositions of the invention include soft surfaces, non-limiting examples of which include: carpets, rugs, upholstery, curtains and drapes, fabrics, textiles, garments, and the like The treatment compositions may also be dispensed, e.g. to a surface, by means of a mist generator means. Such a mist generator means typically includes an element or member which operates to comminute the unpressurized liquid treatment composition into small particles which form a mist, e.g. nebulize or atomize the unpressurized liquid treatment composition. Such a mist generator means may also be considered an aerosol delivery system which is however not generated from a device wherein the treatment composition also includes a propellant constituent. The mist generator means may comprise a vibrating member which includes a metal or ceramic plate; the plate may be solid or porous, or micropierced in the form of a grid or in the form of one or more segments or slots passing through the vibrating member, and a piezoelectric actuator which, when operated, causes vibratory motion in the vibrating member. Alternately, the mist generator means may be an electrostatic spray device. Alternately the mist generator means may be an ultrasonic nozzle device. Such devices are known to the art. Nonlimiting examples of such mist generators and devices which include such mist generator means include those disclosed in one or more of: U.S. Pat. Nos. 5,743,251, 6,234,167, 6,491,233, 6,501,052, 6,516,796, 6,568,390, 6,640,050, 6,681,998, 6,766,220, 6,772,757, 6,804,458, 6,883,516, 7,229,029, US 2007/0011940. US 2007/0169775, US 2007/0235555, US 2008/00419 272. US 2009/0121043. US 2009/0272818, the entire contents of each of which are herein incorporated by reference thereto.

The mist generator means may be an ultrasonic nozzle device. Such ultrasonic nozzle devices may be obtained from commercial sources, e.g., Sono-Tek, Inc. (Milton, N.Y., USA) as well as Sonaer Inc., (Farmingdale, N.Y., USA) as well as being disclosed in published patent applications, US 2009/0254020, and US 2009/0224066, the contents of which are herein incorporated by reference.

Thus a further aspect of the invention provides a closed container containing the inventive composition as described herein.

As certain embodiments of the invention there are provided processes for the treatment of surfaces, e.g., inanimate hard surfaces and inanimate soft surfaces which method includes the step of: contacting such a surface which is in need of treatment or upon which the presence of one or more undesirable microorganisms are suspected or are known to be present, with an effective amount of a surface treatment composition as described herein to provide a surface treatment benefit thereto, preferably to provide a microbicidal benefit to the surface, particularly against various undesirable microorganisms (sometimes referred to as 'pathogens') including various bacteria, mycobacteria, viruses, and fungi, and particularly preferably against poliovirus type 1 (Sabin) ("PV1"). Such methods require the application of an effective amount of a treatment composition as taught herein to such surfaces, so that the desired microbicidal benefit is imparted to the treated surface. Desirably such an effective amount is a sufficient amount of a treatment composition which will provide at least a 1 $\log_{10}$ (log 10) reduction, more preferably at least, and in order of increasing preference, a 1.25, 1.5, 1.75, 2, 2.25, 2.5, 2.75, 3, 3.25, 3.5, 3.75, 4, 4.25, 4.5, 4.75, and 5 log 10 ($\log_{10}$) reduction or even greater degree of $\log_{10}$ reduction against poliovirus type 1 (Sabin) ("PV1") in accordance with one or more of the testing protocols described hereinafter, and/or degrees of microbicidal efficacy of poliovius type 1 (Sabin) or other challenge microorganism, as are demonstrated with reference to one or more of the Examples. Preferred embodiments of the invention provide bactericidal and/or funigicidal and/or mycobactericidal and/or virucidal benefits to treated inanimate surfaces.

With reference to the Examples described later, and with reference to Tables C and 1, the disclosed compositions were subjected to one or more of the following test protocols in order to evaluate their microbicidal efficacy against one or more of the other challenge microorganisms which are identified on Table B. As is known in the art, amongst the most difficult to control or eradicate are non-enveloped viruses, such as poliovirus type 1 (Sabin,) and while microbicidal efficacy against the poliovirus type 1 (Sabin) presumptively demonstrates that the same composition would be expected to be effective against the bacteria and the other non-enveloped viruses disclosed on Table B, the converse is not expected to be true by a skilled artisan. Thus, for example, while a composition which exhibits good microbicidal efficacy against a Gram-positive or Gram-negative bacteria, such would not be expected to be particularly effective against the poliovirus type 1 (Sabin), while the converse would be expected to be true. Further, even demonstrated efficacy of a composition against relatively easier to control or eradicate non-enveloped viruses, such as the rotaviruses, or human adenovirus would not necessarily be expected by a skilled artisan to be particularly effective against the poliovirus type 1 (Sabin), while the converse would be expected to be true.

Preferred and particularly preferred treatment compositions of the invention demonstrate a microbicidal benefit when tested according to the standardized protocol outlined in ASTM E1052 Standard Test Method for Efficacy of Antimicrobial Agents against Viruses in Suspension. This test is per se, known to the art. Preferred treatment compositions exhibit a microbicidal benefit against one, but preferably against two or more of the following challenge organisms, specifically "challenge" non-enveloped viruses: hepatitis A (supplied as hepatitis A virus, strain MH-75 ex. Dr. Mark Sobsey, University of North Carolina, Chapel Hill, N.C.; human adenovirus type 5 (supplied as ATCC VR-5); feline calicivirus strain F-9 (supplied as ATCC VR-782); herpes simplex type 1 (supplied as ATCC VR-1493); human rhinovirus type 14 strain 1059 (supplied as ATCC VR-284), and especially preferably against poliovirus type 1 (Sabin) (supplied by U.S. Centers for Disease Control and Prevention (CDC)), in accordance with this test protocol. As is known to the skilled artisan, of these forgoing challenge viruses, the most resistant to control or eradicate is the poliovirus type 1 (Sabin) and it is commonly presumed that any composition which shows an effective degree of control or eradication against the poliovirus type 1 (Sabin) virus will exhibit an even greater degree of control or eradication of the further prior listed viruses. As is known from the literature, e.g., *Hierarchy of susceptibility of viruses to environmental surface disinfectants: a predictor of activity against new and emerging viral pathogens*. J. AOAC International 90:1655-1658, Sattar, S. A. (2007) the efficacy of a composition in controlling or eradicating poliovirus type 1 (Sabin) provides an excellent prediction of the composition's efficacy against further challenge non-enveloped viruses.

Preferred treatment compositions of the invention demonstrate a microbicidal benefit when tested according to the standardized protocol outlined in ASTM E1053 Standard Test Method to Assess Virucidal Activity of Chemicals Intended for Disinfection of Inanimate. Nonporous Environmental Surfaces. This test is also, per se, known to the art. Preferred treatment compositions exhibit a microbicidal benefit against poliovirus type 1 (Sabin) (supplied by U.S. Centers for Disease Control and Prevention (CDC)), in accordance with this test protocol. Again, as is known to the skilled artisan, of these forgoing challenge viruses the most resistant to control or eradication is the poliovirus type 1 (Sabin) and is it commonly presumed that any composition which shows an effective degree of control or eradication against the poliovirus type 1 (Sabin) will exhibit an even greater degree of control or eradication of many other viruses, including hepatitis A virus, feline calicivirus strain F-9, Herpes simplex type 1 and human rhinovirus type 14 strain 1059 as identified above.

Preferred treatment compositions of the invention demonstrate a microbicidal benefit when tested according to the standardized protocol outlined in European Standard Surface Test, EN13697. This test too is, per se, known to the art. Preferred treatment compositions exhibit a microbicidal benefit against one or more of the following bacteria or fungi: *Staphylococcus aureus* (supplied as ATCC 6538); *Escherichia coli* (supplied as ATCC 10536); *Pseudomonas aeruginosa* (supplied as ATCC 15442); *Enterococcus hirae* (supplied as ATCC 10541) and/or the fungus, *Aspergillus niger* (supplied as ATCC 16404) and/or the fungus *Trichophyton mentagrophytes* (supplied as ATCC 9533) in accordance with the protocols of the test.

Certain preferred treatment compositions of the invention also demonstrate a microbicidal benefit when tested according to the standardized protocol identified as the AOAC Germicidal Spray Products as Disinfectant Test Method, AOAC Index, $17^{th}$ Ed. (2000). This test is also, per se, known to the art. Preferred treatment compositions exhibit a microbicidal benefit against one or more of the following bacteria or fungi: *Staphylococcus aureus* ("*S. aureus*" or "Sa") (supplied as ATCC 6538); *Escherichia coli* ("*E. coli*", or "Ec") (supplied as ATCC 10536), in accordance with the protocols of the test.

The following examples below illustrate exemplary formulations as well as preferred embodiments of the invention. It is to be understood that these examples are provided by way of illustration only and that further useful formulations falling within the scope of the present invention and the claims may be readily produced by one of ordinary skill in the art without deviating from the scope and spirit of the invention.

EXAMPLES

A number of treatment compositions as well as a number of comparative compositions were produced and are described on the following Tables. In these identified compositions, the constituents were used "as supplied" from their respective suppliers and may constitute less than 100% wt. "actives", or may have been supplied as constituting 100% wt. "active" of the named compound, as indicated below. The identified "as supplied" constituent was used, and the "% wt." of each such constituent is indicated on the tables. Treatment compositions which are considered to fall within the scope of the present invention are identified by a digit prepended with the letter "E" which indicates this to be an "example" composition, while compositions provided only for the purposes of comparison are identified by a digit prepended with the letter "C", which indicates this to be a comparative composition and falling outside of the scope of the present invention. In certain of the treatment compositions, one or more constituents, e.g, a pH adjusting agent, or deionized water was added in "quantum sufficient" "q.s." in order to provide a desired pH or to provide a sufficient mass in order to provide 100% wt. of each composition. The example compositions disclosed hereinafter include certain presently preferred embodiments of the invention. The comparative compositions are presented on Table C, while treatment compositions of the invention are identified on one or more of the further tables, e.g, Table 1.

The compositions disclosed on the following tables were produced by simple mixing, under stirring, of the identified constituents, generally in accordance with the following protocol. To a suitably sized laboratory beaker outfitted with a mechanical stirrer or a magnetic stirrer, was first supplied a major proportion of the deionized water. All of the constituents, as well as the laboratory beaker were at room temperature (approx. 20° C.) and as the beaker was open, mixing was at normal atmospheric pressure. Thereafter under stirring conditions (approx. 300 rpm) was added the source of zinc ions, and mixing continued until this material was dissolved. Stirring continued for a further 15-30 minutes to ensure a homogenous mixture, to which was next added the alcohol constituent. Subsequently were added any remaining constituents including any further quantity of pH adjusting constituents (if present) in order to establish the desired pH of the surface treatment composition. Constituents identified as being added "q.s." were added in order to adjust the pH of the formed composition or to bring the weight of the formed composition to 100% wt. Stirring continued for a further 1-15 minutes to ensure the formation of a homogenous mixture, after which the surface treatment composition was withdrawn from the beaker and used or tested.

These compositions as identified below were formed using the constituents identified on the following Table A which identifies the specific constituents used.

TABLE A

| | Constituents |
|---|---|
| zinc citrate · $3H_2O$ | zinc citrate · $3H_2O$, powder, 100% actives |
| zinc acetate | zinc acetate, powder, 100% actives |
| zinc sulfate · $7H_2O$ | zinc sulfate · $7H_2O$, powder, 100% actives |
| zinc chloride | zinc chloride, powder, 100% actives |
| ethanol (100%) | ethanol, technical grade,100% wt. actives |
| BTC-65 (50%) | $C_{12}$-$C_{16}$ alkyl dimethyl benzyl ammonium chloride provided in an aqueous alcoholic carrier (50% wt. actives) (ex. Stepan) |
| Onyxide 3300 (33%) | quaternary ammonium complex with saccharinate counterion, (33% wt. actives, balance ethanol) (ex. Stepan Co.) |
| Neodol 91-6 | nonionic surfactant, $C_9$-$C_{11}$ linear primary alcohol ethoxylate, avg. 6 mols. ethoxylation, 100% wt. actives (ex. Shell Chemical) |
| Crodasol WS | nonionic surfactant based on alcohol alkoxylates, comprising polyethylene glycol monooctyl ether: $CH_3(CH_2)_6CH_2(OCH_2CH_2)_nOH$ where n = 2-8 (100% wt. active) ex. Croda |
| monoethanolamine | monoethanolamine, technical grade (100% wt. active) (ex. Huntsman) |
| triethanolamine | triethanolamine, technical grade (100% wt, active) (ex. Dow Chemical Company) |
| sodium citrate · $2H_2O$ | sodium citrate · $2H_2O$, powder, 100% actives |
| Citrosol 502 (50%) | aqueous solution of citric acid (50% wt, active) (ex. ADM) |
| NH4OH (29.86%) | aqueous solution of NH4OH (29.6% wt. active) |
| NaOH (10%) | aqueous solution of sodium hydroxide, 10% wt. active |
| Trilon BX | aqueous solution of tetrasodium ethylene diamine tetraacetic acid 38.9% wt. actives) (ex. BASF) |
| Monacor BE | borate ester blend, used as supplied (ex. Croda) |
| fragrance | Fragrance, proprietary composition of its supplier |
| di $H_2O$ | deionized water, (100% wt. active) |

Further, wherein a specific composition was evaluated for microbicidal efficacy against a challenge microorganism according to one or more of the test protocols identified above, the results of these tests are reported as well. Wherein multiple challenge microorganisms were evaluated in any one test, multiple results are reported.

The tested microorganisms and their identity as reported on the following Table B:

TABLE B

| | Microorganisms |
|---|---|
| Identifier | Type/Challenge microorganism |
| "PV1" | Virus/Poliovirus type 1 Sabin, ex. supplied by U.S. Centers for Disease Control and Prevention (CDC) |
| "IV-A" | Virus/Influenza A virus, A/California/04/2009 (H1N1), supplied as Biodefence and Emerging Infections Research Resources Repository (BEI Resource) NR-13658 |
| "HAdV" | Virus/Human adenovirus type 5, supplied as ATCC VR-5 |
| "FCV" | Virus/Feline calicivirus strain F-9, supplied as ATCC VR-782 |
| "HSV" | Virus/Herpes simplex type 1, supplied as ATCC VR-1493 |
| "*S. aureus*" or "Sa" | Bacteria/*Staphylococcus aureus*, supplied as ATCC 6538 |
| "*E. coli*" or "Ec" | Bacteria/*Escherichia coli*, supplied as ATCC 10536 |
| "*P. aeruginosa*" or "Pa" | Bacteria/*Pseudomonas aeruginosa* ("*P. aeruginosa*") (supplied as ATCC 15442); |
| "*E. hirae*", or "Eh" | Bacteria/*Enterococcus hirae*, supplied as ATCC 10541 |
| "*A. niger*" | Fungus/*Aspergillis niger*, supplied as ATCC 16404 |
| "*T. ment*" | Fungus/*Trichophyton metagropytes*, supplied as ATCC 9533 |
| "*M. bovis*" | Pathogen/*Mycobacterium tuberculosis* var. *bovis* |

In the following tables, Table C describes various "comparative" examples, (which may be identified by the prepended letter "C") while subsequent Table 1 describes various examples of compositions according to the invention, (which may also be identified by the prepended letter "E") as well as the observed physical properties and the results of microbidical testing according to one or more of the following standardized test protocols:

A) ASTM E1052 Standard Test Method for Efficacy of Antimicrobial Agents against Viruses in Suspension, (for a 5 minute contact time, unless specified otherwise) identified on the following tables as "ASTM E 1052 ($log_{10}$ reduction)";

B) ASTM E1053 Standard Test Method to Assess Virucidal Activity of Chemicals Intended for Disinfection of Inanimate, Nonporous Environmental Surfaces, (for a 5 minute contact time, unless specified otherwise) identified on the following tables as "ASTM 1053 (log 10 reduction)", C) European Standard Surface Test, EN13697, (for a 5 minute contact time, unless specified otherwise) identified on the following tables as "EN 13697 (log 10 reduction)", D) AOAC Germicidal Spray Products as Disinfectant Test Method, AOAC Index, 17th Ed. (2000), (for a 5 minute contact time, unless specified otherwise) identified on the following tables as "AOAC Germicidal Spray". In this test, a result of "0/60" or "1/60" is equivalent to a result of "pass" according to that test's protocols. Results of "2" excess thereof for "/60" tested plates/samples are considered as being equivalent to a "fail" according to that test's protocols.

E) The European Standard Surface Test, EN13697 protocol (for a 15 minute contact time, unless specified otherwise) identified on the following tables as "EN 13697 T.ment" was used for testing antifungal efficacy against *Trichophyton mentagrophytes* or *Aspergillis niger*; the results reported on the tables as the log 10 reduction of the identified fungus.

It is noted that each tested composition was not necessarily tested according to all of the foregoing protocols as, test results of microbicidal efficacy against Poliovirus type 1 Sabin supports the presumption of efficacy against easier to control or eradicate microorganisms.

In the following tables the amount of the zinc ions present are also indicated in parts per million (ppm) and this number is based on the empirical calculation of the available metal ions present in the indicated composition and 100% disassociation of the zinc ion from the zinc ion source is presumed for this empirical calculation.

All of the compositions of both Table 1 and C were liquids which were readily pourable and pumpable and had a "water-thin" viscosity.

All of the compositions of both Tables 1 and C were colorless, and transparent.

TABLE C (Comparative Examples)

| | C1 | C2 | C3 | C4 | C5 | C6 | C7 |
|---|---|---|---|---|---|---|---|
| zinc acetate | — | — | — | 0.08 | — | — | — |
| zinc sulfate•7$H_2O$ | — | — | 0.08 | — | 0.08 | — | — |
| zinc chloride | — | — | — | — | — | — | — |
| ethanol (100%) | 35.0 | 45.0 | — | — | — | — | — |
| BTC-65 (50%) | — | — | — | — | — | 0.20 | — |
| Onyxide 3300 (33%) | — | — | — | — | — | — | 0.30 |
| Neodol 91-6 | — | — | 0.10 | — | — | — | — |
| monoethanolamine | — | — | 0.06 | — | 0.07 | — | — |
| triethanolamine | 0.025 | 0.005 | 0.10 | 0.07 | 0.10 | — | 0.005 |
| sodium citrate•2H2O | — | — | 0.10 | 0.20 | 0.10 | — | — |
| Citrasol 502 (50%) | — | — | 0.05 | — | 0.08 | — | — |
| NH4OH (29.86%) | — | — | — | 0.05 | — | — | — |
| NaOH (10%) | — | — | — | — | — | — | — |
| Triton BX | — | — | — | — | — | — | — |
| Monacor BE | — | — | — | — | — | — | — |
| Silwet Hydrostable | — | — | — | — | — | — | — |
| fragrance | — | — | — | — | — | — | — |
| di $H_2O$ | q.s. | q.s. | q.s. | q.s. | q.s. | q.s. | q.s. |
| pH | 9.23 | 8.70 | 9.03 | 9.33 | 9.18 | 8.58 | 9.16 |
| zinc ions (ppm) | 0 | 0 | 182 | 285 | 182 | 0 | 0 |
| ASTM E 1052 (log10 reduction) | PV1 = 1.83<br>FCV ≥ 6.00 | PV1 ≥ 3.17 | PV1 = 2.83 | PV1 = 2.17 | PV1 = 2.83 | PV1 = 1.83<br>IVA ≥ 5.00<br>HSV ≥ 6.00<br>HAdV = 1.50 | PV1 = 2.50 |
| ASTM 1053 (log10 reduction) | — | — | — | — | — | — | — |
| AOAC Germicidal Spray | Sa = 60/60<br>Pa = 0/60 | — | — | — | — | Sa = 1/60<br>Pa = 1/60 | — |
| EN 13697 (log10 reduction) | Sa = 4.60<br>Ec = 4.19<br>Pa ≥ 4.52<br>Eh ≥ 6.68 | — | — | — | — | Sa = 4.47<br>Ec = 4.28<br>Pa ≥ 4.52<br>Eh = 3.83 | — |
| EN 13697 *T. ment* (log10 reduction) | *A. niger* = 0.93<br>*T. ment* = 4.84 | — | — | — | — | *A. niger* = 0.85<br>*T. ment* = 2.73 | — |

| | C8 | C9 | C10 | C11 | C12 | C13 | C14 | C15 |
|---|---|---|---|---|---|---|---|---|
| zinc acetate | 0.08 | 0.08 | — | — | — | — | — | — |
| zinc sulfate•7$H_2O$ | — | — | 0.08 | — | — | — | — | — |
| zinc chloride | — | — | — | — | — | — | — | — |
| ethanol (100%) | — | — | — | 20.0 | 35.0 | 45.0 | 45.0 | 45.0 |
| BTC-65 (50%) | 0.20 | 0.20 | — | — | 0.20 | 0.20 | — | 0.20 |
| Onyxide 3300 (33%) | — | — | 0.30 | 0.30 | — | — | 0.303 | — |
| Neodol 91-6 | 0.10 | 0.10 | — | 0.10 | 0.10 | 0.10 | — | 0.10 |
| monoethanolamine | 0.05 | — | 0.06 | 0.05 | — | — | — | — |
| triethanolamine | — | 0.27 | 0.10 | 0.10 | 0.016 | 0.01 | 0.005 | — |
| sodium citrate•2H2O | — | — | 0.10 | 0.08 | — | — | — | 0.04 |
| Citrasol 502 (50%) | 0.012 | — | 0.06 | 0.07 | — | — | — | — |
| NH4OH (29.86%) | — | 0.12 | — | — | — | — | — | — |
| NaOH (10%) | — | — | — | — | — | — | — | — |
| Triton BX | — | — | — | — | — | — | — | — |
| Monacor BE | — | — | — | — | — | — | — | — |
| Silwet Hydrostable | — | — | — | — | — | — | — | — |
| fragrance | — | — | — | — | — | — | — | — |
| di $H_2O$ | q.s. | q.s. | q.s. | q.s. | q.s. | q.s. | q.s. | q.s. |
| pH | 8.15 | 8.66 | 9.13 | 9.05 | 8.89 | 7.99 | 8.03 | 8.78 |
| zinc ions (ppm) | 285 | 182 | 0 | 0 | 0 | 0 | 0 | |
| ASTM E 1052 (log10 reduction) | PV1 = 2.17 | PV1 = 1.83 | PV1 = 2.67 | PV1 = 2.83 | PV1 = 2.17 | PV1 = 2.00 | PV1 = 2.00 | PV1 = 3.00 |
| ASTM 1053 (log10 reduction) | — | — | — | — | — | — | — | — |
| AOAC Germicidal Spray | — | — | — | — | — | — | — | — |
| EN 13697 (log10 reduction) | Sa = 3.90<br>Ec ≥ 6.06<br>Pa ≥ 5.41<br>Eh ≥ 6.66 | Sa = 5.01<br>Ec ≥ 6.06<br>Pa ≥ 5.41<br>Eh ≥ 6.66 | — | — | Sa ≥ 6.35<br>Ec ≥ 5.35<br>Pa ≥ 3.85 | — | — | — |
| EN 13697 *T. ment* (log10 reduction) | =1.40 | =1.09 | — | — | *A. niger* = 1.86 | — | — | — |

TABLE C-continued (Comparative Examples)

| | C16 | C17 | C18 |
|---|---|---|---|
| zinc acetate | — | — | — |
| zinc sulfate•7$H_2O$ | — | — | — |
| zinc chloride | — | — | — |
| ethanol (100%) | 45.0 | 55.0 | 70.0 |
| BTC-65 (50%) | — | 0.20 | — |
| Onyxide 3300 (33%) | 0.303 | — | 0.30 |
| Neodol 91-6 | — | 0.10 | 0.10 |
| monoethanolamine | — | 0.06 | 0.05 |
| triethanolamine | 0.03 | 0.10 | 0.10 |
| sodium citrate•2H2O | — | 0.10 | 0.08 |
| Citrasol 502 (50%) | — | 0.06 | 0.07 |
| NH4OH (29.86%) | — | — | — |
| NaOH (10%) | — | — | — |
| Triton BX | — | — | — |
| MEA-MIPA bonate | — | — | — |
| Monacor BE | — | — | — |
| Silwet Hydrostable | — | — | — |
| fragrance | — | — | — |
| di $H_2O$ | q.s. | q.s. | q.s. |
| pH | 8.9 | 9.03 | 9.14 |
| zinc ions (ppm) | 0 | 0 | 0 |
| ASTM E 1052 (log10 reduction) | PV1 = 2.27 | PV1 = 4.00 | PV1 = 5.83 |
| ASTM 1053 (log10 reduction) | — | — | — |
| AOAC Germicidal Spray | — | — | — |
| EN 13697 (log10 reduction) | Sa ≥ 6.75<br>Ec ≥ 6.06<br>Pa ≥ 5.41<br>Eh ≥ 6.66 | — | — |
| EN 13697 *T. ment* (log10 reduction) | ≥4.61 | — | — |

| | C19 | C20 | C21 | C22 | C23 | C24 |
|---|---|---|---|---|---|---|
| zinc acetate | — | — | — | — | — | — |
| zinc sulfate•7$H_2O$ | — | — | — | — | — | — |
| zinc chloride | — | — | — | — | — | — |
| ethanol (100%) | 49.77 | 49.77 | 49.77 | 49.77 | 49.77 | 49.77 |
| BTC-65 (50%) | — | — | — | — | — | — |
| Onyxide 3300 (33%) | 0.337 | 0.337 | 0.337 | 0.337 | 0.337 | 0.337 |
| Neodol 91-6 | — | — | — | — | — | — |
| monoethanolamine | 0.02 | — | — | 0.13 | 0.65 | 2.51 |
| triethanolamine | 0.1 | 0.1 | 0.1 | 0.1 | 0.1 | 0.1 |
| sodium citrate•2$H_2O$ | — | — | — | — | — | — |
| Citrasol 502 (50%) | 0.35 | 0.26 | 0.19 | 0.12 | 0.12 | 0.12 |
| NH4(OH) (29.86%) | 0.1 | 0.1 | 0.1 | 0.1 | 0.1 | 0.1 |
| NaOH (10%) | — | — | — | — | — | — |
| Trilon BX | — | — | — | — | — | — |
| Monacor BE | 0.15 | 0.15 | 0.15 | 0.15 | 0.15 | 0.15 |
| Crodasol WS | 0.15 | 0.15 | 0.15 | 0.15 | 0.15 | 0.15 |
| fragrance | — | — | — | — | — | — |
| di $H_2O$ | q.s. | q.s. | q.s. | q.s. | q.s. | q.s. |
| pH | 9.0 | 9.25 | 9.53 | 10.0 | 10.5 | 10.99 |
| zinc ions (ppm) | 0 | 0 | 0 | 0 | 0 | 0 |
| ASTM E 1052 (log10 reduction), 5 minute contact time | PV1 = 2.17 | PV1 = 2.56 | PV1 = 2.83 | PV1 = 2.83 | PV1 = 2.96 | PV1 = 3.17 |
| ASTM 1053 (log10 reduction), 5 minute contact time | — | — | — | PV1 = 0.27 | PV1 = 0.44 | PV1 = 0.27 |
| ASTM 1053 (log10 reduction), 30 seconds contact time | — | — | — | PV1 = 0.44 | PV1 = 1.10 | PV1 = 2.27 |

TABLE 1

(Example Compositions)

| | E1 | E2 | E3 | E4 | E5 | E6 | E7 |
|---|---|---|---|---|---|---|---|
| zinc acetate | — | — | 0.08 | 0.08 | 0.08 | | |
| zinc sulfate•7$H_2O$ | 0.10 | 0.12 | — | — | — | 0.12 | 0.12 |
| zinc chloride | — | — | — | — | — | — | — |
| ethanol (100%) | 20.0 | 35.0 | 35.0 | 35.0 | 35.0 | 38.0 | 38.0 |
| BTC-65 (50%) | — | — | 0.20 | 0.20 | — | — | — |
| Onyxide 3300 (33%) | 0.30 | 0.303 | — | — | — | 0.303 | 0.303 |
| Neodol 91-6 | 0.10 | 0.10 | 0.10 | 0.10 | 0.10 | 0.10 | 0.10 |

TABLE 1-continued

| (Example Compositions) | | | | | | | |
|---|---|---|---|---|---|---|---|
| monoethanolamine | 0.20 | — | — | 0.74 | — | — | — |
| triethanolamine | 0.10 | 0.15 | 0.07 | — | 0.07 | 0.15 | — |
| sodium citrate•2$H_2O$ | 0.08 | 0.20 | 0.20 | — | 0.20 | — | 0.20 |
| Citrasol 502 (50%) | 0.32 | — | — | — | — | 0.09 | — |
| NH4OH (29.86%) | — | 0.17 | 0.06 | — | 0.07 | 0.13 | 0.08 |
| NaOH (10%) | — | — | — | — | — | — | — |
| Triton BX | — | — | — | — | — | — | — |
| MEA-MIPA borate | — | — | — | — | — | — | — |
| Monacor BE | — | — | — | — | — | — | — |
| Silwet Hydrostable | — | — | — | — | — | — | — |
| fragrance | — | — | — | — | — | — | — |
| di $H_2O$ | q.s. | q.s. | q.s. | q.s. | q.s. | q.s. | q.s. |
| pH | 9.03 | 9.50 | 9.05 | 10.76 | 9.11 | 9.28 | 9.46 |
| zinc ions (ppm) | 227.4 | 272.8 | 285 | 285 | 285 | 272.8 | 272.8 |
| ASTM E 1052 (log10 reduction) | PV1 = 2.50 | PV1 = 3.30 | PV1 = 2.17 | PV1 ≥ 5.00 | PV1 = 2.00 | PV1 = 2.33 | PV1 = 3.00 |
| ASTM 1053 (log10 reduction) | — | — | — | — | — | — | — |
| AOAC Germicidal Spray | — | — | — | — | — | — | — |
| EN 13697 (log10 reduction) | — | — | Sa ≥ 6.75<br>Ec ≥ 6.06<br>Pa ≥ 5.41<br>Eh ≥ 6.66 | — | Sa ≥ 6.75<br>Ec ≥ 6.06<br>Pa ≥ 5.41<br>Eh ≥ 6.66 | — | — |
| EN 13697 *T. ment* (log10 reduction) | — | — | ≥4.61 | — | ≥4.61 | — | — |

| | E8 | E9 | E10 | E11 | E12 | E13 | E14 |
|---|---|---|---|---|---|---|---|
| zinc acetate | — | — | — | — | — | — | — |
| zinc sulfate•7$H_2O$ | 0.08 | 0.08 | 0.08 | 0.08 | 0.08 | 0.08 | 0.08 |
| zinc chloride | — | — | — | — | — | — | — |
| ethanol (100%) | 40.0 | 40.0 | 40.0 | 40.0 | 40.0 | 40.0 | 40.0 |
| BTC-65 (50%) | — | — | — | — | — | — | — |
| Onyxide 3300 (33%) | — | — | 0.300 | 0.30 | 0.15 | 0.15 | 0.30 |
| Neodol 91-6 | — | 0.10 | 0.10 | 0.10 | 0.10 | 0.10 | 0.10 |
| monoethanolamine | 0.06 | 0.07 | 0.008 | 0.015 | 0.06 | 0.80 | 0.70 |
| triethanolamine | 0.10 | 0.10 | 0.10 | 0.10 | 0.10 | 0.10 | 0.10 |
| sodium citrate•2H2O | 0.10 | — | 0.20 | 0.20 | 0.10 | 0.10 | 0.20 |
| Citrasol 502 (50%) | 0.05 | 0.05 | 0.015 | — | 0.05 | 0.05 | — |
| NH4OH (29.86%) | — | — | — | — | — | 0.08 | 0.15 |
| NaOH (10%) | — | — | — | — | — | — | — |
| Triton BX | — | — | — | — | — | — | — |
| MEA-MIPA borate | — | — | — | — | — | — | — |
| Monacor BE | — | — | — | — | — | — | — |
| Silwet Hydrostable | — | — | — | — | — | — | — |
| fragrance | — | — | — | — | — | — | — |
| di $H_2O$ | q.s. | q.s. | q.s. | q.s. | q.s. | q.s. | q.s. |
| pH | 9.00 | 9.13 | 8.52 | 9.13 | 9.05 | 10.73 | 11.0 |
| zinc ions (ppm) | 182 | 182 | 182 | 182 | 182 | 182 | 182 |
| ASTM E 1052 (log10 reduction) | PV1 = 2.56 | PV1 = 2.73 | PV1 = 2.50 | PV1 = 2.83 | PV1 = 3.00 | PV1 ≥ 6.00 | PV1 ≥ 5.00 |
| ASTM 1053 (log10 reduction) | — | — | — | — | — | — | — |
| AOAC Germicidal Spray | — | — | — | — | — | — | — |
| EN 13697 (log10 reduction) | — | — | Sa ≥ 6.75<br>Ec ≥ 6.06<br>Pa ≥ 5.41<br>Eh ≥ 6.66 | — | — | — | — |
| EN 13697 *T. ment* (log10 reduction) | — | — | ≥4.61 | — | — | — | — |

| | E15 | E16 | E17 | E18 | E19 | E20 | E21 | E22 |
|---|---|---|---|---|---|---|---|---|
| zinc acetate, 3$H_2O$ | 0.10 | 0.10 | — | — | — | — | — | 0.15 |
| zinc sulfate•7$H_2O$ | — | — | 0.115 | 0.115 | 0.115 | 0.12 | 0.12 | — |
| zinc chloride | — | — | — | — | — | — | — | — |
| ethanol (100%) | 40.0 | 40.0 | 40.0 | 40.0 | 40.0 | 40.0 | 43.0 | 40.0 |
| BTC-65 (50%) | 0.40 | 0.40 | — | — | — | — | — | 0.20 |
| Onyxide 3300 (33%) | — | — | 0.303 | 0.91 | 0.30 | 0.30 | 0.303 | — |
| Neodol 91-6 | 0.10 | 0.10 | 0.10 | 0.10 | 0.10 | 0.10 | 0.10 | 0.10 |
| monoethanolamine | — | — | — | — | — | 0.04 | — | — |
| triethanolamine | 0.34 | 0.38 | 0.72 | 0.38 | 0.38 | 0.10 | 0.15 | 0.38 |
| sodium citrate•2$H_2O$ | — | — | — | — | — | 0.20 | — | — |
| Citrasol 502 (50%) | 0.07 | 0.07 | 0.15 | 0.19 | 0.19 | — | 0.02 | 0.08 |
| NH4OH (29.86%) | — | 0.15 | — | 0.08 | 0.07 | — | 0.12 | — |
| NaOH (10%) | — | 0.45 | — | 0.25 | 0.42 | — | — | — |
| Triton BX | — | — | — | — | — | — | — | — |
| MEA-MIPA borate | — | — | — | 0.20 | 0.41 | — | — | — |
| Monacor BE | — | — | — | — | — | — | — | — |
| Silwet Hydrostable | — | — | — | — | — | — | — | — |
| fragrance | — | — | — | — | — | — | — | — |
| di $H_2O$ | q.s. | q.s. | q.s. | q.s. | q.s. | q.s. | q.s. | q.s. |

TABLE 1-continued (Example Compositions)

| | | | | | | | | |
|---|---|---|---|---|---|---|---|---|
| pH | 7.92 | 11.02 | 7.92 | 9.72 | 10.35 | 9.10 | 9.46 | 7.89 |
| zinc ions (ppm) | 310 | 310 | 261 | 261 | 261 | 272.8 | 278 | 465 |
| ASTM E 1052 (log10 reduction) | PV1 = 2.00 | PV1 ≥ 5.00 | PV1 = 2.50 | PV1 ≥ 4.73 | PV1 ≥ 5.00 | PV1 = 2.17 | PV1 = 3.92 | PV1 = 2.00 |
| ASTM 1053 (log10 reduction) | — | — | — | — | — | — | — | — |
| AOAC Germicidal Spray | — | — | — | — | — | — | — | — |
| EN 13697 (log10 reduction) | — | — | — | — | — | — | — | — |
| EN 13697 *T. ment* (log10 reduction) | — | — | — | — | — | — | — | — |

| | E23 | E24 | E25 | E26 | E27 | E28 | E29 | E30 |
|---|---|---|---|---|---|---|---|---|
| zinc acetate | — | 0.08 | 0.08 | 0.08 | — | — | 0.08 | 0.08 |
| zinc sulfate•7$H_2O$ | 0.12 | — | — | — | — | — | — | — |
| zinc chloride | — | — | — | — | 0.055 | 0.055 | — | — |
| ethanol (100%) | 43.0 | 45.0 | 45.0 | 45.0 | 45.0 | 45.0 | 45.0 | 45.0 |
| BTC-65 (50%) | — | — | — | — | — | — | — | — |
| Onyxide 3300 (33%) | 0.303 | — | — | 0.303 | 0.303 | 0.303 | 0.303 | 0.303 |
| Neodol 91-6 | 0.10 | 0.10 | 0.10 | 0.10 | 0.10 | 0.10 | 0.10 | 0.10 |
| monoethanolamine | — | — | 0.02 | — | — | — | — | — |
| triethanolamine | 0.15 | 0.12 | 0.27 | 0.22 | 0.38 | 0.38 | 0.22 | 0.295 |
| sodium citrate•2$H_2O$ | 0.20 | 0.20 | — | — | — | — | — | — |
| Citrasol 502 (50%) | 0.02 | — | 0.14 | 0.27 | 0.15 | 0.12 | 0.145 | 0.13 |
| NH4OH (29.86%) | 0.12 | 0.03 | 0.12 | — | 0.30 | 0.30 | 0.15 | 0.26 |
| NaOH (10%) | — | — | — | — | — | — | — | — |
| Triton BX | — | — | — | — | — | — | — | — |
| MEA-MIPA borate | — | — | — | — | — | 0.10 | 0.06 | — |
| Monacor BE | — | — | — | — | — | — | — | — |
| Silwet Hydrostable | — | — | — | — | — | — | — | — |
| fragrance | — | — | — | — | — | — | — | — |
| di $H_2O$ | q.s. | q.s. | q.s. | q.s. | q.s. | q.s. | q.s. | q.s. |
| pH | 9.46 | 8.05 | 8.74 | 6.07 | 8.34 | 9.27 | 9.25 | 9.45 |
| zinc ions (ppm) | 272.8 | 285 | 285 | 285 | 263.8 | 263.8 | 285 | 285 |
| ASTM E 1052 (log10 reduction) | PV1 = 3.92 | PV1 = 2.50 | PV1 ≥ 5.00 | PV1 = 1.75 | PV1 = 2.27 | PV1 ≥ 4.73 | PV1 ≥ 5.00 | PV1 = 4.50 |
| ASTM 1053 (log10 reduction) | — | — | — | — | — | — | — | — |
| AOAC Germicidal Spray | — | — | — | — | — | — | Sa = 0/30<br>Pa = 0/30 | — |
| EN 13697 (log10 reduction) | — | — | Sa ≥ 6.75<br>Ec ≥ 6.06<br>Pa ≥ 5.41<br>Eh ≥ 6.66 | — | — | — | Sa ≥ 6.75<br>Ec ≥ 6.06<br>Pa ≥ 5.41<br>Eh ≥ 6.66 | — |
| EN 13697 *T. ment* (log10 reduction) | — | — | ≥4.61 | — | — | — | ≥4.61 | — |

| | E31 | E32 | E33 | E34 | E35 | E36 | E37 | E38 |
|---|---|---|---|---|---|---|---|---|
| zinc acetate | 0.08 | 0.08 | 0.08 | 0.08 | 0.08 | 0.08 | 0.08 | 0.08 |
| zinc sulfate•7$H_2O$ | — | — | — | — | — | — | — | — |
| zinc chloride | — | — | — | — | — | — | — | — |
| ethanol (100%) | 45.0 | 45.0 | 45.0 | 45.0 | 45.0 | 45.0 | 45.0 | 45.0 |
| BTC-65 (50%) | — | 0.20 | 0.20 | 0.20 | — | — | — | 0.20 |
| Onyxide 3300 (33%) | — | — | — | — | — | 0.303 | 0.303 | — |
| Neodol 91-6 | 0.10 | 0.10 | 0.10 | 0.10 | 0.10 | 0.10 | 0.10 | 0.10 |
| monoethanolamine | — | — | — | — | 0.02 | 0.11 | 0.11 | 0.75 |
| triethanolamine | 0.12 | 0.27 | 0.22 | 0.335 | 0.27 | 0.22 | 0.22 | 0.07 |
| sodium citrate•2$H_2O$ | 0.20 | — | — | — | — | — | — | 0.20 |
| Citrasol 502 (50%) | — | 0.14 | 0.21 | — | 0.14 | 0.155 | 0.14 | — |
| NH4OH (29.86%) | 0.03 | 0.08 | 0.14 | — | 0.12 | 0.124 | 0.124 | 0.17 |
| NaOH (10%) | — | — | — | — | — | — | — | — |
| Triton BX | — | — | — | 0.26 | — | — | — | — |
| MEA-MIPA borate | — | — | — | — | — | 0.08 | — | — |
| Monacor BE | — | — | — | — | — | — | — | — |
| Silwet Hydrostable | — | — | — | — | — | — | — | — |
| fragrance | — | — | — | — | — | — | — | — |
| di $H_2O$ | q.s. | q.s. | q.s. | q.s. | q.s. | q.s. | q.s. | q.s. |
| pH | 8.05 | 8.09 | 8.56 | 8.6 | 8.74 | 9.63 | 9.63 | 10.78 |
| zinc ions (ppm) | 285 | 285 | 285 | 285 | 285 | 285 | 285 | 285 |
| ASTM E 1052 (log10 reduction) | PV1 = 2.50 | PV1 = 3.50 | PV1 = 3.83 | PV1 ≥ 5.50 | PV1 ≥ 5.00 | PV1 ≥ 4.50 | PV1 ≥ 4.50 | PV1 ≥ 5.00 |
| ASTM 1053 (log10 reduction) | — | — | — | — | — | — | — | — |
| AOAC Germicidal Spray | — | — | — | — | — | — | — | — |
| EN 13697 (log10 reduction) | — | — | Sa ≥ 6.75<br>Ec = 4.98<br>Pa ≥ 5.41<br>Eh ≥ 6.66 | — | Sa ≥ 6.75<br>Ec ≥ 6.06<br>Pa ≥ 5.41<br>Eh ≥ 6.66 | — | — | — |
| EN 13697 *T. ment* (log10 reduction) | — | — | ≥4.61 | — | ≥4.61 | — | — | — |

TABLE 1-continued (Example Compositions)

| | E39 | E40 | E41 | E42 | E43 |
|---|---|---|---|---|---|
| zinc acetate | 0.08 | — | — | — | — |
| zinc sulfate•$7H_2O$ | — | 0.10 | 0.10 | 0.115 | 0.115 |
| zinc chloride | — | — | — | — | — |
| ethanol (100%) | 45.0 | 55.0 | 70.0 | 45.0 | 45.0 |
| BTC-65 (50%) | — | 0.20 | — | — | — |
| Onyxide 3300 (33%) | 0.303 | — | 0.30 | 0.303 | 0.30 |
| Neodol 91-6 | 0.10 | 0.10 | 0.10 | 0.10 | 0.10 |
| monoethanolamine | — | 0.075 | 0.15 | — | — |
| triethanolamine | 0.27 | 0.10 | 0.10 | 0.35 | 0.40 |
| sodium citrate•$2H_2O$ | — | 0.10 | 0.08 | — | — |
| Citrasol 502 (50%) | 0.14 | 0.06 | 0.20 | 0.14 | 0.19 |
| NH4OH (29.86%) | — | — | — | 0.09 | 0.13 |
| NaOH (10%) | — | — | — | — | — |
| Triton BX | — | — | — | — | — |
| MEA-MIPA borate | — | — | — | — | 0.20 |
| Monacor BE | — | — | — | — | — |
| Silwet Hydrostable | — | — | — | — | — |
| fragrance | — | — | — | — | — |
| di $H_2O$ | q.s. | q.s. | q.s. | q.s. | q.s. |
| pH | 7.08 | 9.03 | 9.2 | 8.14 | 9.5 |
| zinc ions (ppm) | 285 | 227.4 | 227.4 | 261 | 261 |
| ASTM E 1052 (log10 reduction) | PV1 = 3.17 | PV1 = 4.17 | PV1 ≥ 6.00 | PV1 = 1.50 | PV1 ≥ 4.73 |
| ASTM 1053 (log10 reduction) | — | — | — | — | — |
| AOAC Germicidal Spray | — | — | — | — | — |
| EN 13697 (log10 reduction) | — | — | — | — | — |
| EN 13697 *T. ment* (log10 reduction) | — | — | — | — | — |

| | E44 | E45 | E46 | E47 | E48 | E49 | E50 |
|---|---|---|---|---|---|---|---|
| zinc acetate | — | — | — | — | — | — | — |
| zinc sulfate•$7H_2O$ | 0.13 | 0.13 | 0.13 | 0.13 | 0.13 | 0.13 | 0.13 |
| zinc chloride | — | — | — | — | — | — | — |
| ethanol (100%) | 43.0 | 43.0 | 43.0 | 43.0 | 43.0 | 43.0 | 43.0 |
| BTC-65 (50%) | — | — | — | — | — | — | — |
| Onyxide 3300 (33%) | 0.33 | 0.33 | 0.33 | 0.33 | 0.33 | 0.33 | 0.33 |
| Neodol 91-6 | 0.10 | 0.10 | 0.10 | 0.10 | 0.10 | 0.10 | 0.10 |
| monoethanolamine | 1.04 | 1.04 | 1.04 | 1.04 | 1.04 | 1.04 | 1.04 |
| triethanolamine | 0.10 | 0.10 | 0.10 | 0.10 | 0.10 | 0.10 | 0.10 |
| sodium citrate | — | — | — | — | — | — | — |
| Citrasol 502 (50%) | 0.12 | 0.12 | 0.12 | 0.12 | 0.12 | 0.12 | 0.12 |
| NH4OH (29.86%) | 0.10 | 0.10 | 0.10 | 0.10 | 0.10 | 0.10 | 0.10 |
| NaOH (10%) | — | — | — | — | — | — | — |
| Triton BX | — | — | — | — | — | — | — |
| Monacor BE | 0.065 | 0.10 | 0.15 | 0.25 | — | — | — |
| sodium benzoate | — | — | — | — | 0.06 | 0.10 | 0.15 |
| Silwet Hydrostable | — | — | — | — | — | — | — |
| fragrance | — | — | — | — | — | — | — |
| di $H_2O$ | q.s. | q.s. | q.s. | q.s. | q.s. | q.s. | q.s. |
| pH | 10.55 | 10.54 | 10.52 | 10.45 | 10.58 | 10.55 | 10.51 |
| zinc ions (ppm) | — | — | — | — | — | — | — |
| ASTM E 1052 (log10 reduction) | PV1 ≥ 7.00 | PV1 ≥ 7.00 | PV1 ≥ 7.00 | PV1 ≥ 7.00 | PV1 ≥ 7.00 | PV1 ≥ 7.00 | PV1 ≥ 7.00 |
| ASTM 1053 (log10 reduction) | — | — | — | — | — | — | — |
| AOAC Germicidal Spray | — | — | — | — | — | — | — |
| EN 13697 (log10 reduction) | — | — | — | — | — | — | — |
| EN 13697 *T. ment* (log10 reduction) | — | — | — | — | — | — | — |

| | E51 | E52 | E53 | E54 | E55 | E56 |
|---|---|---|---|---|---|---|
| zinc acetate | — | — | — | — | — | — |
| zinc sulfate•$7H_2O$ | 0.14 | 0.14 | 0.14 | 0.14 | 0.14 | 0.14 |
| zinc chloride | — | — | — | — | — | — |
| ethanol (100%) | 49.77 | 49.77 | 49.77 | 49.77 | 49.77 | 49.77 |
| BTC-65 (50%) | — | — | — | — | — | — |
| Onyxide 3300 (33%) | 0.337 | 0.337 | 0.337 | 0.337 | 0.337 | 0.337 |
| Neodol 91-6 | — | — | — | — | — | — |
| monoethanolamine | — | 0.01 | — | 0.34 | 1.4 | 4.92 |
| triethanolamine | 0.1 | 0.1 | 0.1 | 0.1 | 0.1 | 0.1 |
| sodium citrate•$2H_2O$ | — | — | — | — | — | — |
| Citrasol 502 (50%) | 0.27 | 0.18 | 0.12 | 0.12 | 0.12 | 0.12 |
| NH4(OH) (29.86%) | 0.1 | 0.1 | 0.1 | 0.1 | 0.1 | 0.1 |
| NaOH (10%) | — | — | — | — | — | — |
| Trilon BX | — | — | — | — | — | — |
| Monacor BE | 0.15 | 0.15 | 0.15 | 0.15 | 0.15 | 0.15 |
| Crodasol WS | 0.15 | 0.15 | 0.15 | 0.15 | 0.15 | 0.15 |

TABLE 1-continued (Example Compositions)

| | | | | | | |
|---|---|---|---|---|---|---|
| fragrance | — | — | — | — | — | — |
| di $H_2O$ | q.s. | q.s. | q.s. | q.s. | q.s. | q.s. |
| pH | 9.0 | 9.25 | 9.50 | 10.0 | 10.51 | 11.03 |
| zinc ions (ppm) | 318.33 | 318.33 | 318.33 | 318.33 | 318.33 | 318.33 |
| ASTM E 1052 (log10 reduction), 5 minute contact time | PV1 = 6.5 | PV1 ≥ 6.83 | PV1 ≥ 6.83 | PV1 ≥ 6.83 | PV1 ≥ 6.83 | PV1 ≥ 6.83 |
| ASTM 1053 (log10 reduction), 30 seconds contact time | — | — | PV1 = 2.77 | PV1 = 3.33 | PV1 ≥ 4.73 | PV1 ≥ 4.73 |
| ASTM 1053 (log10 reduction), 5 minutes contact time | — | PV1 = 3.27 | PV1 ≥ 4.27 | PV1 ≥ 4.27 | PV1 ≥ 4.27 | PV1 ≥ 4.27 |

| | E57 | E58 | E59 | E60 | E61 | E62 | E63 | E64 |
|---|---|---|---|---|---|---|---|---|
| zinc acetate | — | — | — | — | — | — | — | — |
| zinc sulfate•$7H_2O$ | 0.14 | 0.14 | 0.14 | 0.14 | 0.14 | 0.14 | 0.14 | 0.14 |
| zinc chloride | — | — | — | — | — | — | — | — |
| ethanol (100%) | 35.0 | 35.0 | 35.0 | 35.0 | 40.0 | 40.0 | 40.0 | 40.0 |
| BTC-65 (50%) | — | — | — | — | — | — | — | — |
| Onyxide 3300 (33%) | — | — | — | — | — | — | — | — |
| Neodol 91-6 | 0.1 | 0.1 | 0.1 | 0.1 | 0.1 | 0.1 | 0.1 | 0.1 |
| monoethanolamine | — | — | — | — | 0.07 | 0.07 | 0.07 | 0.07 |
| triethanolamine | 0.07 | 0.07 | 0.07 | 0.07 | 0.1 | 0.1 | 0.1 | 0.1 |
| sodium citrate | 0.2 | 0.2 | 0.2 | 0.2 | 0.1 | 0.1 | 0.1 | 0.1 |
| Citrasol 502 (50%) | — | — | — | — | 0.05 | 0.05 | 0.05 | 0.05 |
| NH4OH (29.86%) | 0.07 | 0.07 | 0.07 | 0.07 | — | — | — | — |
| NaOH (10%) | 0.07 | 0.13 | 0.16 | 0.18 | 0.06 | 0.17 | 0.25 | 0.32 |
| Triton BX | — | — | — | — | — | — | — | — |
| Monacor BE | — | — | — | — | — | — | — | — |
| sodium benzoate | — | — | — | — | — | — | — | — |
| Silwet Hydrostable | — | — | — | — | — | — | — | — |
| fragrance | — | — | — | — | — | — | — | — |
| di $H_2O$ | q.s. | q.s. | q.s. | q.s. | q.s. | q.s. | q.s. | q.s. |
| pH | 9.99 | 10.51 | 11.04 | 11.5 | 9.46 | 9.98 | 10.5 | 11.51 |
| zinc ions (ppm) | 318.33 | 318.33 | 318.33 | 318.33 | 318.33 | 318.33 | 318.33 | 318.33 |
| ASTM 1053 (log10 reduction) | PV1 = 2.33 | PV1 = 3.5 | PV1 = 5.33 | PV1 = 5.5 | PV1 = 2 | PV1 = 1.67 | PV1 = 3.5 | PV1 = 4.77 |

| | E65 | E66 | E67 | E68 | E69 | E70 | E71 | E72 | E73 |
|---|---|---|---|---|---|---|---|---|---|
| zinc acetate | — | — | — | — | — | — | — | — | — |
| zinc sulfate•$7H_2O$ | 0.14 | 0.14 | 0.14 | 0.14 | 0.14 | 0.14 | 0.14 | 0.14 | 0.14 |
| zinc chloride | — | — | — | — | — | — | — | — | — |
| ethanol (100%) | 42.5 | 42.5 | 42.5 | 42.5 | 42.5 | 45.0 | 45.0 | 45.0 | 45.0 |
| BTC-65 (50%) | — | — | — | — | — | — | — | — | — |
| Onyxide 3300 (33%) | — | — | — | — | — | — | — | — | — |
| Neodol 91-6 | 0.1 | 0.1 | 0.1 | 0.1 | 0.1 | 0.1 | 0.1 | 0.1 | 0.1 |
| monoethanolamine | — | — | — | — | — | 0.2 | 0.2 | 0.2 | 0.2 |
| triethanolamine | 0.15 | 0.15 | 0.15 | 0.15 | 0.15 | 0.27 | 0.27 | 0.27 | 0.27 |
| sodium citrate | — | — | — | — | — | — | — | — | — |
| Citrasol 502 (50%) | 0.2 | 0.02 | 0.02 | 0.02 | 0.02 | 0.65 | 0.29 | 0.14 | 0.14 |
| NH4OH (29.86%) | 0.12 | 0.12 | 0.12 | 0.12 | 0.12 | 0.12 | 0.12 | 0.12 | 0.12 |
| NaOH (10%) | 0.06 | 0.04 | 0.22 | 0.37 | 0.5 | — | — | 0.32 | 0.47 |
| Triton BX | — | — | — | — | — | — | — | — | — |
| Monacor BE | — | — | — | — | — | — | — | — | — |
| sodium benzoate | — | — | — | — | — | — | — | — | — |
| Silwet Hydrostable | — | — | — | — | — | — | — | — | — |
| fragrance | — | — | — | — | — | — | — | — | — |
| di $H_2O$ | q.s. | q.s. | q.s. | q.s. | q.s. | q.s. | q.s. | q.s. | q.s. |
| pH | 8.49 | 9.5 | 10.0 | 10.5 | 11.5 | 8.51 | 9.53 | 10.46 | 10.98 |
| zinc ions (ppm) | 318.33 | 318.33 | 318.33 | 318.33 | 318.33 | 318.33 | 318.33 | 318.33 | 318.33 |
| ASTM 1053 (log10 reduction) | PV1 = 2.44 | PV1 = 1.67 | PV1 ≥ 5.17 | PV1 ≥ 5.17 | PV1 ≥ 5.17 | PV1 = 1.67 | PV1 = 2.0 | PV1 ≥ 5.17 | PV1 ≥ 5.17 |

As can be seen from the foregoing results the compositions of the invention exhibited excellent microbicidal efficacy as demonstrated by the various test results, even wherein reduced amounts of ethanol were present as a constituent.

With respect to the reported results of microbicidal efficacy as reported on the foregoing Tables, it is to be understood that each of the identified test protocols were performed according to their published standardized protocols, and the results are reported according to the identified test protocols. For example in the ASTM E 1052, ASTM 1053, EN 131697 tests, the use of the symbol "≥" (greater-than-or-equal-to) indicated that the $\log_{10}$ reduction of the challenge microorganism was at least equal to the reported result, but may be greater, while the use of the symbol "=" or the lack of a mathematical operator symbol indicated that the $\log_{10}$ reduction of the challenge microorganism was at least as indicated. In the AOAC Germicidal Spray test, the reported results indicate the number of positive substrates/total substrates, e.g., a result of "0/60" indicates that no positive substrates (survivors) were present within the 60 substrate samples tested.

The invention claimed is:

1. A transparent liquid, inanimate surface treatment composition which imparts a virucidal benefit to treated surfaces which composition comprises:

0.001 -2.5% wt. of a zinc ion source material which releases zinc ions into the treatment composition;

at least 35% wt. of at least one lower alkyl aliphatic monohydric alcohol, and wherein ethanol is the predominant alcohol present in the lower alkyl aliphatic monohydric alcohol constituent;

water;

optionally, one or more further constituents which impart one or more advantageous technical or aesthetic benefits to the compositions;

wherein the composition has a pH of at least 6.07, wherein any quaternary ammonium compounds which impart a germicidal benefit are not present in the composition; and wherein the surface treatment compositions are characterized in exhibiting at least a 2 $\log_{10}$ reduction of poliovirus type 1 (Sabin) when tested according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces.

2. A transparent liquid, inanimate surface treatment composition which imparts a virucidal benefit to such treated surfaces which compositions comprises:

0.001 -2.5% wt. of a zinc ion source material which releases zinc ions into the treatment composition;

in excess of 0% wt., and up to but excluding 20% wt of at least one lower alkyl aliphatic monohydric alcohol, and wherein ethanol is the predominant alcohol present in the lower alkyl aliphatic monohydric alcohol constituent;

water;

optionally, one or more further constituents which impart one or more advantageous technical or aesthetic benefits to the compositions;

wherein the composition has a pH of at least 5, wherein any quaternary ammonium compounds which impart a germicidal benefit are not present in the composition; and wherein the surface treatment compositions are characterized in exhibiting a at least a 2 $\log_{10}$ reduction of poliovirus type 1 (Sabin), when tested according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces.

3. A composition according to claim 2, wherein the composition exhibits a pH of at least 6.07.

4. A composition according to claim 1 wherein ethanol is the sole alcohol present in the lower aliphatic monohydric alcohol constituent.

5. A composition according to claim 1, wherein the composition concurrently satisfies at least one of the following Conditions A, B, C, D, E, F, G, H, I, J, K, L, M, and N:

| Condition | pH or pH range | % wt. of at least one lower alkyl aliphatic monohydric alcohol | $\log_{10}$ reduction of poliovirus type 1 (Sabin) ("PV1") when tested according to the standardized test protocol: ASTM E1052 |
|---|---|---|---|
| A | >8.5 | ≥40 and ≤45.2 | at least 1.5 |
| B | ≥8.5 to <9 | ≥40 and ≤45.2 | at least 2.5 |
| C | ≥9 to <9.5 | ≥35 and ≤70.2 | at least 0.5 |
| D | ≥9.5 to <10 | ≥35 and ≤50 | at least 3.3 |
| E | ≥10 to <10.5 | ≥40 and ≤50 | at least 5.0 |
| F | ≥10.5 to <11 | ≥35 and ≤50 | at least 5.0 |
| G | ≥11 | ≥35 and ≤50 | at least 5.0 |
| H | >8.5 | ≥40 and ≤45.2 | — |
| I | ≥8.5 to <9 | ≥40 and ≤45.2 | at least 1.67 |
| J | ≥9 to <9.5 | ≥35 and ≤70.2 | at least 2 |
| K | ≥9.5 to <10 | ≥35 and ≤50 | at least 1.67 |
| L | ≥10 to <10.5 | ≥40 and ≤50 | at least 3.3 |
| M | ≥10.5 to <11 | ≥35 and ≤50 | at least 3.5 |
| N | ≥11 | ≥35 and ≤50 | at least 4.27. |

6. A composition according to claim 1, wherein the composition concurrently satisfies at least one of the following Conditions O, P, Q, R, and S:

| Condition | % wt. of at least one lower alkyl aliphatic monohydric alcohol | pH or pH range | $\log_{10}$ reduction of poliovirus type 1 (Sabin) ("PV1") when tested according to the standardized test protocol: ASTM E1052 |
|---|---|---|---|
| O | ≥35 and <40 | ≥9.03 and ≤10.76 | at least 2.0 |
| P | ≥40 and <45 | ≥7.92 and ≤11.51 | at least 2.0 |
| Q | ≥45 and <50 | ≥6.07 and ≤11.5 | at least 1.5 |
| R | ≥50 | ≥9.03 and ≤9.2 | at least 4.17 |
| S | ≥35 and <40 | ≥9.03 and ≤10.76 | —. |

7. A method of controlling the incidence of undesired microorganisms on an inanimate surface, the method comprising the step of: contacting the inanimate surface which is in need of treatment or upon which the presence of one or more undesirable microorganisms are suspected or are known to be present, with an effective amount of a composition according to claim 1, to provide a virucidal benefit to the contacted surface.

8. A liquid, inanimate surface treatment composition according to claim 1, wherein the zinc ion source material which releases $Zn^{++}$ions into the treatment composition.

9. A liquid, inanimate surface treatment composition according to claim 2, wherein the zinc ion source material which releases $Zn^{++}$ions into the treatment composition.

10. A liquid, inanimate surface treatment composition according to claim 1, wherein the composition contains:

at least about 35% wt. and up to but less than 42.5% wt. of the lower alkyl mononhydric alcohol constituent; and, has a pH of about 9 to about 11.5.

11. A liquid, inanimate surface treatment composition according to claim 1, wherein the composition contains:

42.5% wt. and up to about 45% wt. of the lower alkyl mononhydric alcohol constituent; and, has a pH of about 8 to about 11.5.

* * * * *